US008674317B2

(12) United States Patent
Hatakeyama et al.

(10) Patent No.: US 8,674,317 B2
(45) Date of Patent: *Mar. 18, 2014

(54) SAMPLE SURFACE INSPECTION APPARATUS AND METHOD

(75) Inventors: Masahiro Hatakeyama, Kanagawa (JP); Kenji Watanabe, Kanagawa (JP); Takeshi Murakami, Tokyo (JP); Tohru Satake, Kanagawa (JP); Nobuharu Noji, Kanagawa (JP)

(73) Assignee: Ebara Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/289,486

(22) Filed: Nov. 4, 2011

(65) Prior Publication Data
US 2012/0049063 A1 Mar. 1, 2012

Related U.S. Application Data

(62) Division of application No. 12/153,397, filed on May 19, 2008, now Pat. No. 8,076,654, which is a division of application No. 10/511,396, filed as application No. PCT/JP03/04910 on Apr. 17, 2003, now Pat. No. 7,391,036.

(30) Foreign Application Priority Data

Apr. 17, 2002 (JP) .................................. 2002-114756
May 1, 2002 (JP) .................................. 2002-129515

(51) Int. Cl.
*G21K 7/00* (2006.01)
(52) U.S. Cl.
USPC ......... 250/396 R; 250/397; 250/306; 250/307
(58) Field of Classification Search
USPC ............. 250/305, 306, 307, 310, 311, 396 R, 250/397; 430/296
See application file for complete search history.

(56) References Cited

U.S. PATENT DOCUMENTS 4,978,855 A 12/1990 Liebl et al.
5,045,696 A * 9/1991 Hirose .............................. 850/9

(Continued)

FOREIGN PATENT DOCUMENTS

DE 39 04 032 A1 8/1990
EP 1 313 126 A2 5/2003

(Continued)

OTHER PUBLICATIONS

International Search Report dated Aug. 5, 2003, issued in corresponding International Application No. PCT/JP03/04910.

(Continued)

*Primary Examiner* — Nicole Ippolito
(74) *Attorney, Agent, or Firm* — Westerman, Hattori, Daniels & Adrian, LLP

(57) ABSTRACT

The present invention provides a surface inspection method and apparatus for inspecting a surface of a sample, in which a resistive film is coated on the surface, and a beam is irradiated to the surface having the resistive film coated thereon, to thereby conduct inspection of the surface of the sample. In the surface inspection method of the present invention, a resistive film having an arbitrarily determined thickness $t_1$ is first coated on a surface of a sample. Thereafter, a part of the resistive film having the arbitrarily determined thickness $t_1$ is dissolved in a solvent, to thereby reduce the thickness of the resistive film to a desired level. This enables precise control of a value of resistance of the resistive film and suppresses distortion of an image to be detected.

11 Claims, 19 Drawing Sheets

(56) References Cited

U.S. PATENT DOCUMENTS

| | | | |
|---|---|---|---|
| 5,464,977 A * | 11/1995 | Nakagiri et al. | 250/234 |
| 5,889,282 A | 3/1999 | Yang et al. | |
| 6,165,552 A | 12/2000 | Anai et al. | |
| 6,183,942 B1 | 2/2001 | Kim et al. | |
| 6,300,043 B1 | 10/2001 | Konishi et al. | |
| 6,407,385 B1 | 6/2002 | Okada | |
| 6,465,781 B1 | 10/2002 | Nishimura et al. | |
| 8,076,654 B2 * | 12/2011 | Hatakeyama et al. | 250/492.1 |
| 2002/0005484 A1 | 1/2002 | Nishimura | |
| 2002/0033449 A1 | 3/2002 | Nakasuji et al. | |
| 2002/0036264 A1 | 3/2002 | Nakasuji et al. | |
| 2002/0054297 A1 * | 5/2002 | Lee et al. | 356/607 |
| 2002/0182760 A1 | 12/2002 | Wack et al. | |
| 2003/0111601 A1 * | 6/2003 | Adler et al. | 250/307 |
| 2003/0116717 A1 | 6/2003 | Knippelmeyer | |
| 2004/0071888 A1 | 4/2004 | Chondroudis et al. | |
| 2005/0206018 A1 | 9/2005 | Ohmi et al. | |

FOREIGN PATENT DOCUMENTS

| | | |
|---|---|---|
| GB | 2 268 802 A | 1/1994 |
| JP | 63-069563 A | 3/1988 |
| JP | 01-221637 A | 9/1989 |
| JP | 01-320421 A | 12/1989 |
| JP | 2-054155 A | 2/1990 |
| JP | 04-163931 A | 6/1992 |
| JP | 6-308061 A | 11/1994 |
| JP | 10-104180 A | 4/1998 |
| JP | 10-208678 | 8/1998 |
| JP | 11-214461 A | 8/1999 |
| JP | 2000-215840 | 8/2000 |
| JP | 2000-215841 | 8/2000 |
| JP | 2000-215842 | 8/2000 |
| JP | 2000-223401 A | 8/2000 |
| JP | 2000-286310 A | 10/2000 |
| JP | 2000-314710 A | 11/2000 |
| JP | 2000-327483 | 11/2000 |
| JP | 2000-353648 A | 12/2000 |
| JP | 2001-083112 A | 3/2001 |
| JP | 2001-267383 A | 9/2001 |
| JP | 2001-272363 A | 10/2001 |
| JP | 2001-307991 A | 11/2001 |
| JP | 2001-522945 A | 11/2001 |
| JP | 2001-007991 A | 12/2001 |
| JP | 2002-016067 A | 1/2002 |
| JP | 2002-075265 A | 3/2002 |
| JP | 2002-148227 A | 5/2002 |
| JP | 2002-262545 A | 9/2002 |
| JP | 2005-512339 A | 4/2005 |
| WO | 99-25004 A1 | 5/1999 |
| WO | 02-13227 A1 | 2/2002 |
| WO | 03-050841 A1 | 6/2003 |

OTHER PUBLICATIONS

ESPACER 300, Technical Data Sheet, Showa Denko.

Supplemental European Search Report dated Nov. 11, 2008, issued in corresponding European Application No. 03720920.2.

Motosuke Miyoshi et al., J. Vac. Scl. Technol. B 19(6), Nov./Dec. 2001, pp. 2852-2855.

Photo-Electron Emission Microscope Model Peemspector, ULVAC-PHI, Inc., (with English translation).

Extended European Search Report dated Jan. 24, 2013, issued in corresponding European Patent Application No. 12007216.0 (8 pages).

* cited by examiner

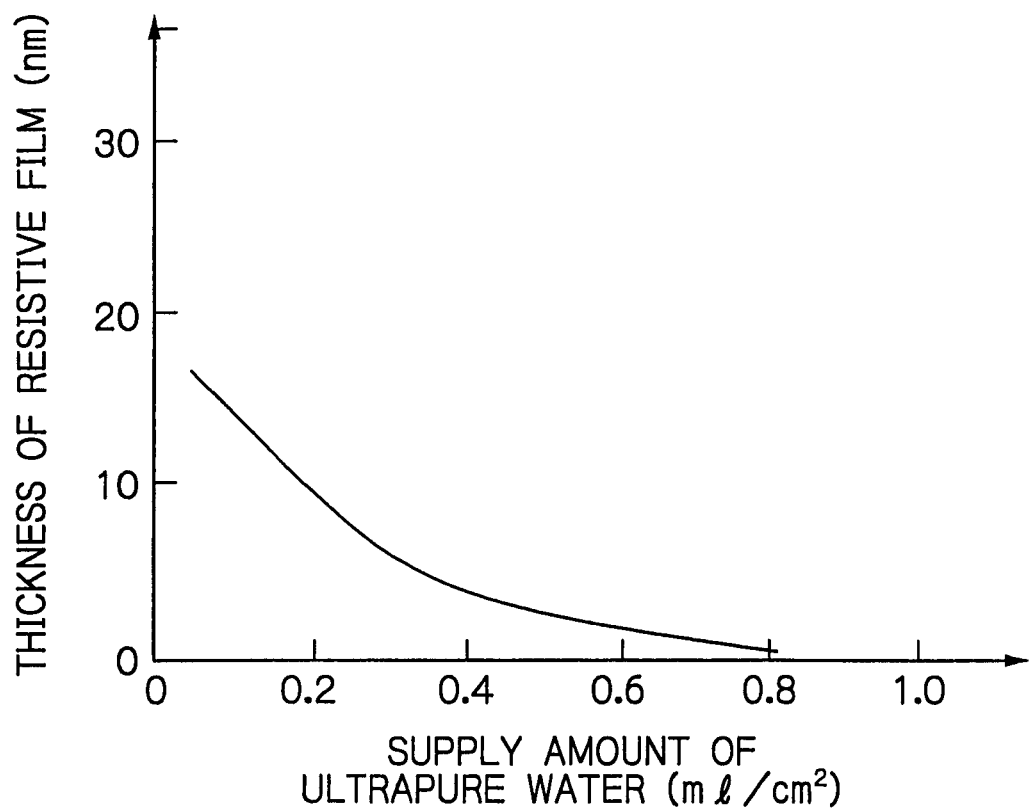

SAMPLE SURFACE INSPECTION APPARATUS AND METHOD

This application is a divisional of U.S. patent application Ser No. 12/153,397, filed May 19, 2008, which is a divisional of U.S. patent application Ser. No. 10/511,396, filed on Mar. 23, 2005, now U.S. Pat. No. 7,391,036, issued Jun. 24, 2008, which is a §371 of International Application No. PCT/JP03/04910 filed on Apr. 17, 2003, which claims the priority of Japanese Application Nos. 114756/2002 and 129515/2002, filed on Apr. 17, 2002 and May 1, 2002, respectively, all of which are incorporated herein by reference.

TECHNICAL FIELD

The present invention relates to a surface inspection apparatus and method for effectively performing evaluations, observations, analyses and the like such a structure inspection, an observation in an enlarged view, a material evaluation, an electric conduction and so forth of a sample surface. More particularly, the present invention relates to a surface inspection apparatus and method which can detect defects on high density patterns having, for example, a minimum line width of 0.15 µm or less on a sample surface, with high accuracy, high reliability and high throughput. The present invention also relates to a semiconductor device manufacturing system which incorporates such a surface inspection apparatus, and a semiconductor device manufacturing method which employs such a surface inspection apparatus to inspect patterns in the midway of a semiconductor device manufacturing process and/or after completion of the process.

BACKGROUND ART

Conventionally, when a surface of a sample, such as a substrate or a wafer, is observed or subjected to material inspection, or is inspected or evaluated with respect to a structure or electric continuity of electric circuits formed thereon, it is known to use a surface inspection apparatus in which a defect in a surface of a sample is detected by emitting a charged particle beam (a primary charged particle beam), such as an electron beam, to the surface for scanning, detecting secondary charged particles emitted from the surface, producing image data from the detected secondary charged particles, and comparing the produced image data with the image data for each die (or chip). Such surface inspection apparatuses including one that utilizes a scanning electron microscope (SEM), and surface flattening apparatuses for flattening a surface of a sample, such as a substrate, exist as independent apparatuses and have been conventionally used.

In such a conventional SEM-based system as described above, and a system which simultaneously illuminates a wide area on a wafer, as a wafer under inspection is irradiated with an electron beam, the wafer is charged. The overcharged wafer Would cause distorted image data and obscure images. In addition, a normal pattern may be erroneously evaluated as defective.

Another grave problem in the prior art is damages to a sample. Specifically, when an electron beam is irradiated to a surface of a wafer, the surface is charged by the irradiated beam, permitting acquisition of an image representative of a potential contrast. However, the wafer may be charged in a different condition depending on insulating material, metal conductive materials, circuit resistance, and the like. Therefore, occasionally, an extreme potential difference may be produced on a boundary of patterns, resulting in failed acquisition of secondary electrons emitted from the wafer surface or in arc discharge.

The above-mentioned problems will be described in greater detail.

Secondary electron emission characteristics differ from one sample to another depending on the energy of an incident irradiated beam thereon and the characteristic of the sample surface. FIG. 1 is a graph showing an exemplary relationship between beam energy and secondary electron emission efficiency η when an insulating material is irradiated with an electron beam. With η larger than one, more electrons than incident electrons are emitted from the insulating material, and hence the surface of the insulating material is positively charged (Region P). On the other hand, with η smaller than one, the surface is negatively charged (Region Q). This may cause damages such as breakdown in some samples, the characteristics of which depend on the circuit configuration and layered structure thereon.

Specifically, when an insulating material is applied with an electric field equal to or larger than a breakdown strength (for example, 50-1000 kV/mn), the insulating material loses the insulating property to cause a breakdown, resulting in a current flowing therethrough. On the other hand, when an excessive amount of charge is accumulated on the insulating material, the field strength exceeds a breakdown voltage, thereby resulting in a breakdown. Also, once a breakdown occurs, an excessive current flows to break the circuit, and the insulating material may no longer restore its insulating property.

Further, when the magnitude of a beam current is decreased so as to minimize distortion of the image data due to the electric charge, an S/N ratio of a signal resulting from a secondary charged particle beam, which is emitted from the surface of the sample by emission of a primary charged particle beam, becomes undesirably low. This increases the possibility of false detection. The problem of lowering of the S/N ratio may be lessened and the possibility of false detection may be reduced, by effecting scanning at a plurality of times and conducting an averaging operation. However, the throughput in such an inspection apparatus becomes low.

Further, in order to detect fine defects, a large-current emission beam is required. For example, when it is assumed that the amount of signal required for determining a defect having a 2×2 pixel size of a CCD is 1, the amount of signal required for determining a defect having a 1×1 pixel size is 4. That is, for detecting a fine defect by using the same detector, the magnitude of a beam current must be increased so as to increase the amount of secondary electrons. However, when the magnitude of a beam current is increased, as is described above, the electric charge on the sample becomes high, thus increasing distortion of the image.

In order to solve the above-mentioned problems, the Applicant proposed, in Japanese Patent Application No. 2000-340651 (published as Japanese Patent Public Disclosure (Kokai) No. 2002-148227), a method in which a resistive film is coated on the surface of a sample before emission of a charged particle beam to the surface. In this method, however, it is difficult to form a thin resistive film having a uniform thickness on each sample. Further improvements are required to be made.

Although a technique of coating a resistive film or coat on the surface of the sample before inspection was proposed by the forgoing application, no proposals have been made with respect to an inspection apparatus which enables a series of operations such as surface flattening, resistive film coating and emission of a charged particle beam for inspection to be efficiently conducted. Conventional independent apparatuses, such as a flattening apparatus for flattening a surface of a sample, a cleaning apparatus for cleaning a sample, and a drying apparatus, are individually placed with a resistive film coating apparatus, and each operation is conducted by using these apparatuses. With this arrangement, however, it is difficult to efficiently conduct the above-mentioned series of operations. The reason for this is as follows. That is, each of the above independent apparatuses comprises a sample loading station and a loading/unloading robot. A sample conveyed by a conveyor apparatus for conveying a sample between the apparatuses is temporarily loaded on the sample loading station. The loading/unloading robot moves the sample from the sample loading station to a work position, i.e., a stage device, and removes the sample from the stage device. A plurality of such independent apparatuses are individually placed and a conveyor apparatus for conveying a sample between the independent apparatuses is further provided. This results in a complicated structure and an increase in overall size of a surface inspection apparatus. Further, the time required for conveying the sample is long and the throughput in the entire apparatus is low. Further, the possibility of contamination and oxidation of a surface of a sample increases, leading to deterioration of product quality.

DISCLOSURE OF THE INVENTION

The present invention has been made to solve the problems in the prior arts as mentioned above, and it is an object of the invention to provide a sample surface inspection apparatus and method, which is capable of reliably performing inspections such as observation, detection of defects, analysis, and the like on a surface of a sample without damaging the sample.

It is another object of the invention to provide a method for forming a resistive film on a sample and a resistive film forming apparatus enabling an amount of electric charge on a sample to be appropriately controlled and enabling clear image data having minimum distortion to be obtained with respect to a surface of the sample, by making the thickness of the resistive film thin.

It is another object of the invention to provide a surface inspection method and a surface inspection apparatus, wherein even when scanning is conducted using a high-current beam so as to increase a throughput, an amount of electric charge on a sample can be appropriately controlled and clear image data having minimum distortion can be obtained with respect to a surface of the sample, thus enabling a defect to be detected by scanning with high reliability.

It is another object of the invention to provide a method and an apparatus for inspecting a surface of a sample with high reliability, wherein the thickness of a resistive film formed on the surface of the sample can be precisely controlled so that a resistive film having a desired thickness can be formed uniformly with respect to each sample, to thereby enable clear image data having minimum distortion to be obtained with respect to the surface of the sample.

It is a further object of the invention to provide a surface inspection system having a simple structure enabled by improving mechanisms for flattening, cleaning and drying a sample, a mechanism for coating a resistive film on a surface of a sample, and a mechanism for conveying a sample between the above mechanisms, while maintaining a high throughput.

It is another object of the invention to provide a surface inspection system which enables a loading/unloading robot of each independent apparatus to be eliminated, thus simplifying the apparatus and a process for conveyance of a sample, and which is capable of maintaining a high throughput.

It is another object of the invention to provide a semiconductor device manufacturing method which employs the surface inspection apparatus to inspect a semiconductor wafer in the middle of or after completion of a process.

In order to achieve the objects, the present invention provides a method of forming a resistive film on a surface of a sample, which comprises the steps of:

rotating the sample at a rotational speed with the sample being held in a substantial horizontal situation;

dropping a liquid film material on the sample surface while the sample is being rotated, to form a resistive film thereon; and dropping a solvent which solves the resistive film formed on the sample surface while the sample is being rotated at a rotational speed, thereby dissolving a part of the resistive film to obtain the resistive film having a desired level of thickness.

In the above method, it is preferable that the desired level of the thickness of the resistive film is 0.1 nm to 10 nm, and the resistive film is water-soluble.

The present invention further provides an apparatus for forming a resistive film on a surface of a sample, which comprises:

a spin coater which drops a liquid film material on the sample surface while the sample is rotated at a rotational speed with the sample being held in a substantial horizontal situation, thereby forming a resistive film on the sample surface; and a film thickness uniformalizing mechanism which makes the thickness of the resistive film formed on the sample surface thin and uniform by dissolving a part of the resistive film with a solvent.

In the above apparatus, it is preferable that the film thickness uniformalizing mechanism includes a solvent dropping device which drops a solvent dissolving the resistive film while the sample is rotated.

The present invention further provides a method of inspecting a surface of a sample, which comprises the steps of;

coating the sample surface with a resistive film having an arbitrarily determined thickness;

dissolving a part of the resistive film, to thereby reduce the thickness of the resistive film to a desired level which is thinner than that of the arbitrarily determined thickness; and irradiating a charged particle beam to the sample surface coated with the resistive film, to thereby conduct inspection of the sample surface.

In the above method, it is preferable that the desired level of the thickness of the resistive film is 0.1 nm to 10 nm, the resistive film is water-soluble, and the method further comprises the step of removing the resistive film from the sample surface by cleaning it with pure water or ultrapure water after the inspection of the sample surface.

The present invention further provides a system for inspecting a surface of a sample, which comprises:

a surface flattening mechanism for flattening the sample surface;

a resistive film coating mechanism for coating a resistive film on the sample surface after the surface is flattened by the surface flattening mechanism, the resistive film having an arbitrarily determined thickness, and then dissolving a part of the resistive film in a solvent, to thereby reduce the thickness of the resistive film to a desired level;

an inspection mechanism for emitting a charged particle beam to the sample surface having the resistive film coated thereon, to thereby conduct inspection of the sample surface; and a conveyor mechanism for conveying the sample between the mechanisms.

In the above system, it is preferable that the system further comprises a cleaning mechanism and a sample drying mechanism so that the sample in a clean and dry state is introduced into and removed from the surface inspection apparatus, wherein the surface flattening mechanism, the resistive film coating mechanism, the inspection mechanism, the cleaning mechanism and the sample drying mechanism are disposed so as to surround the conveyor mechanism.

The present invention further provides a mechanism for inspecting a surface of a sample, comprising:

an electromagnetic wave irradiation apparatus comprising an electromagnetic wave source, and a device for guiding an electromagnetic wave generated from the electromagnetic wave source onto a sample surface;

a detector for detecting electrons emitted from the sample surface which is irradiated with the electromagnetic wave to output an electric or optical signal; and a processing unit for processing the electric or optical signal from the detector for evaluation of the sample surface.

In the above mechanism, it is preferable that the electromagnetic wave source is a source which emits an ultraviolet or X-ray laser, or an ultraviolet ray or X-ray having a wavelength of 400 nm or less. The mechanism could further comprises: an electron beam irradiation apparatus comprising an electron beam source, and a device for guiding an electron beam generated from the electron beam source onto the sample surface; and an apparatus for driving one or both of the electromagnetic wave irradiation apparatus and the electron beam irradiation apparatus to irradiate the sample surface with one or both of the electromagnetic wave or the electron beam. The mechanism could further comprises an imaging optical system for guiding the electrons emitted from the sample surface to the detector.

The present invention further provides a method of manufacturing a semiconductor device comprising the step of inspecting a semiconductor wafer in the middle of a manufacturing process and/or after completion of the manufacturing process, using the inspection apparatus or system as above or by the inspection method as above.

BRIEF DESCRIPTION OF THE DRAWINGS

FIG. 7 is a graph indicating the relationship between the thickness of the resistive film remaining on the wafer and the supply amount of ultrapure water, when the resistive film coated on the wafer is dissolved in ultrapure water under a condition different to that of the case shown in FIG. 5;

BEST MODE FOR CARRYING THE INVENTION

Figure 1:
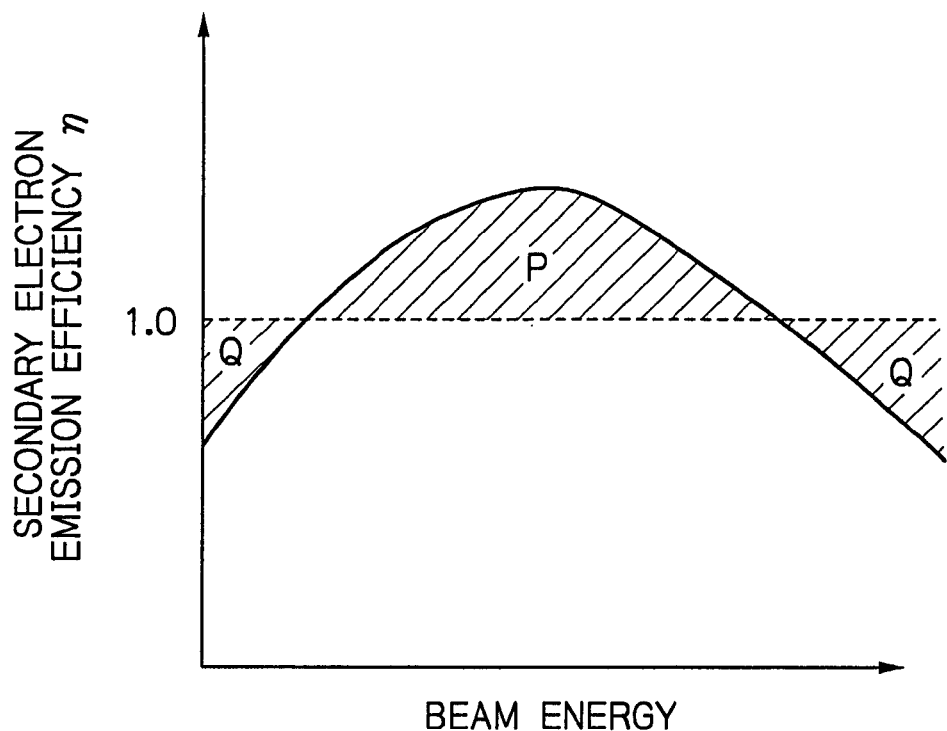
FIG. 1 is a graph showing a relationship between beam energy and secondary electron emission efficiency.

Referring to the drawings, description is made with regard to embodiments of the present invention.

Figure 2:
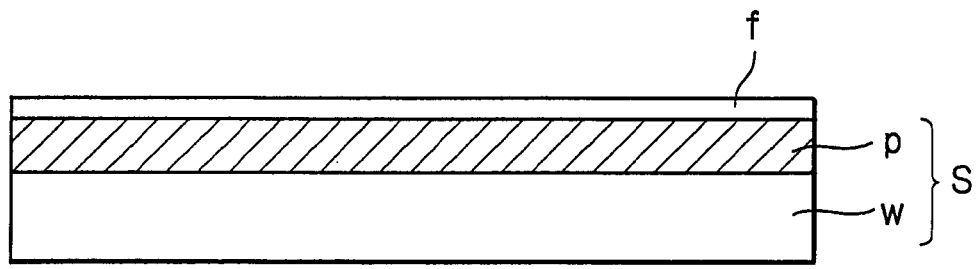
FIG. 2 is a cross-sectional view of a silicon wafer on which a resistive film is coated.

FIG. 2 is an enlarged cross-sectional view showing a sample S to be inspected by a surface inspection method of the present invention. In this embodiment, as the sample S, a silicon wafer (hereinafter, referred to simply as "a wafer") W during a semiconductor device manufacturing process, on which an arbitrarily determined pattern p such as an electronic circuit has been formed, is taken as an example. In an inspection process or some processes for manufacturing semiconductor circuit, an electron beam is emitted to a surface of the wafer W [in the following explanation of this embodiment, an electron beam (a primary electron beam) is taken as an example of a charged particle beam emitted to a wafer], and the resulting electron beam (a secondary electron beam) emitted from the wafer W is detected, to thereby conduct inspection of the surface of the wafer W. Such inspection is conducted to detect foreign matter, a defect in electric continuity, a defect or loss of a pattern, determine a wafer condition or determine the types of wafers for sorting. However, when the magnitude of a current of an electron beam emitted to the wafer W is increased, the electric charge on the wafer W increases, thus generating distortion of image data produced from detected secondary electrons, and preventing accurate detection.

Figure 3:
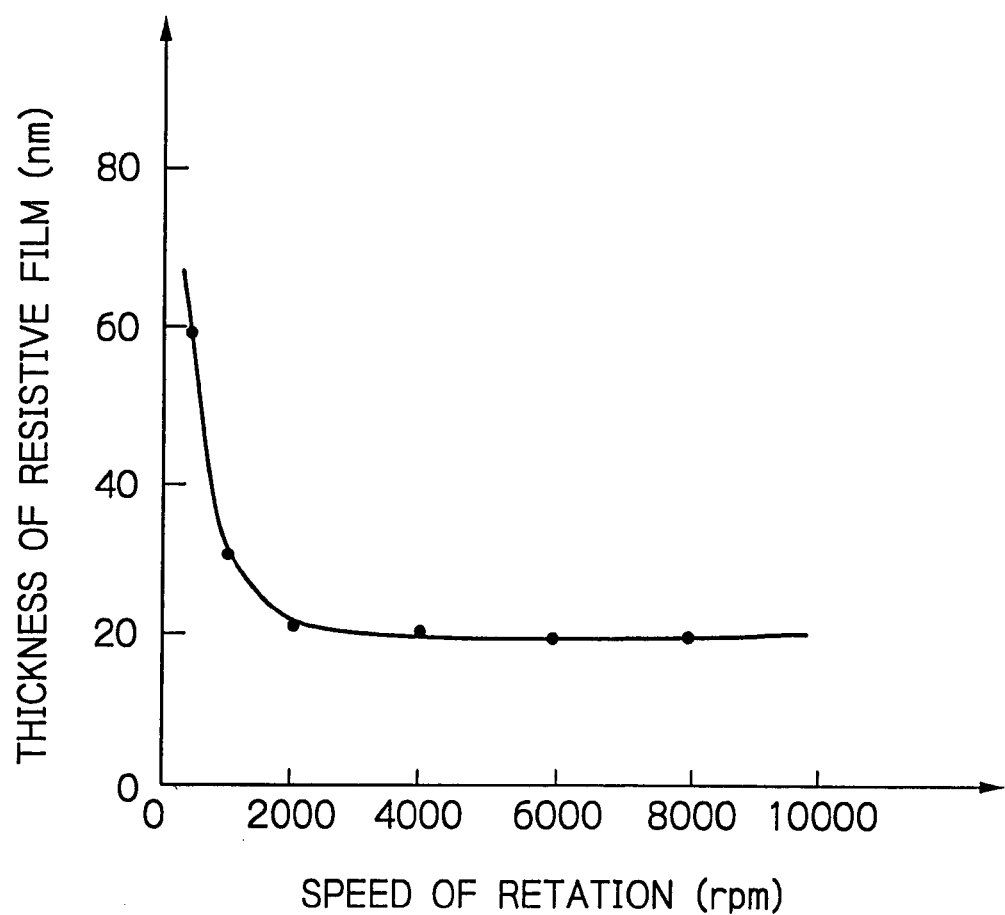
FIG. 3 is a graph indicating the relationship between the speed of rotation (rpm) of a wafer and the thickness of a resistive film formed on the wafer by a spin coater.

In order to solve this problem, in the above-mentioned patent application, the Applicant proposed a method of controlling the amount of electric charge on the wafer by coating a resistive film f on the wafer. However, it was found that the amount of electric charge on the wafer cannot be precisely controlled simply by coating a resistive film on the wafer. That is, when a resistive film is formed by using a so-called spin coater, as is indicated in FIG. 3, the thickness of resistive film becomes small as the speed of rotation (revolutions per minute) of the wafer increases, but the thickness of resistive film does not decrease when the rotation speed of the wafer exceeds a certain level, namely, about 2,000 rpm. In fact, it is impossible to obtain a resistive film having a thickness less than about 20 nm.

As is explained with reference to FIG. 1, with a high beam energy such that η larger than 1, the number of electrons emitted from the insulating material is larger than that of incident electrons. Therefore, the surface of the insulating material is positively charged. The value of resistance and the thickness of a resistive film are herein important. When the value of resistance is as small as that of a metallic film, a potential contrast of the image becomes low, and distortion of the image is suppressed. However, pattern recognition becomes poor and detection of a defect becomes difficult. When the value of resistance is too large, the image is distorted to a large extent. Secondary electrons emitted from a part of the surface cannot be obtained, and arc discharge occurs.

Figure 4A:
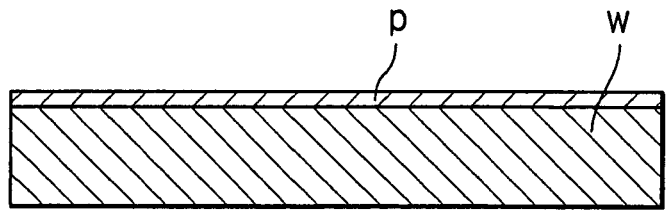
FIGS. 4(A)-4(C) are cross-sectional views for explaining a method for uniformalizing a thickness of a resistive film according to the invention.
Figure 4B:
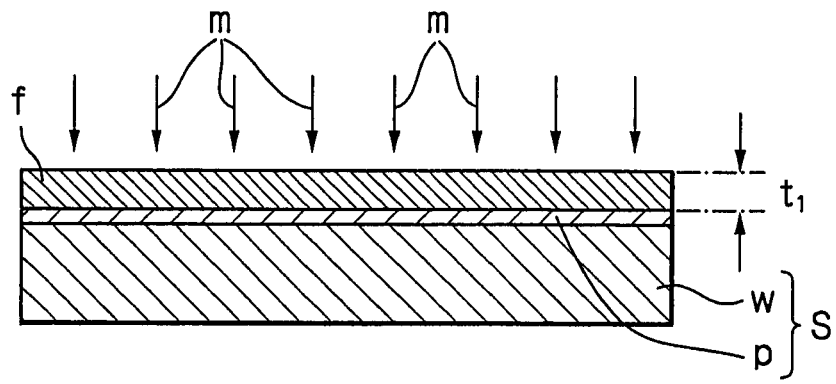

In the present invention, as in conventional techniques, the surface of the wafer W (in this embodiment in which the pattern p is formed on an upper surface of the wafer W, the surface of the layer of pattern p) is flattened, by means of a surface flattening mechanism, such as a CMP (Chemical Mechanical Polishing) apparatus having a structure known in the art or a reactive ion flattening apparatus using plasma (FIG. 4(A)). Subsequently, as shown in FIG. 4(B), a resistive film material m in liquid form is sprayed over the flattened surface of the wafer W while the wafer W is rotated, by a conventional spin coater, to thereby form a resistive film f. Coating is conducted so that the thickness of the resistive film f becomes a thickness $t_1$ which is larger than a desired thickness to be finally obtained. As a resistive film material, use is made of, for example, a metal-containing polymer material or a polymer compound of a thienyl alkane sulphonate type. The value of resistance is about $1\times10^6$ to $100\times10^6\Omega$ (per $cm^2$, for example; a film thickness: 0.1 nm to 100 nm). A resistive film made of a polymer compound of a thienyl alkane sulphonate type is water-soluble, which is advantageous in a film-removing process described later. Instead of a polymer compound of a thienyl alkane sulphonate, similar coating materials of an acrylic type or a chemical amplification type may be used. According to the present invention, by appropriately selecting the value of resistance, image distortion can be minimized and surface inspection can be conducted efficiently while reducing the risk of false detection. When inspection is conducted during an LSI manufacturing process, removability of the resistive film is important because after the inspection, the resistive film must be removed before subjecting the wafer to the subsequent process. Therefore, use of a water-soluble resistive film is of great importance in the present invention.

As is described above, the thickness of a resistive film which can be obtained by a spin coater is limited. In fact, it is impossible to form a resistive film having a thickness less than 20 nm. Therefore, conventionally, a wafer coated with a resistive film having a thickness of 20 nm or more is subjected to inspection.

This is problematic, however, in the following point. That is, when acquiring secondary electrons emitted from the wafer by emission of a primary electron beam, an error in acquisition due to the thickness of the resistive film occurs. For example, when electrons pass through the resistive film, due to lowering of a electric field for extraction, secondary electrons are dispersed, leading to a low contrast and a blur of the image.

To prevent these problems, it is desired to further reduce the thickness of the resistive film. However, as is described above, conventional coating methods are unsatisfactory.

Figure 4C:
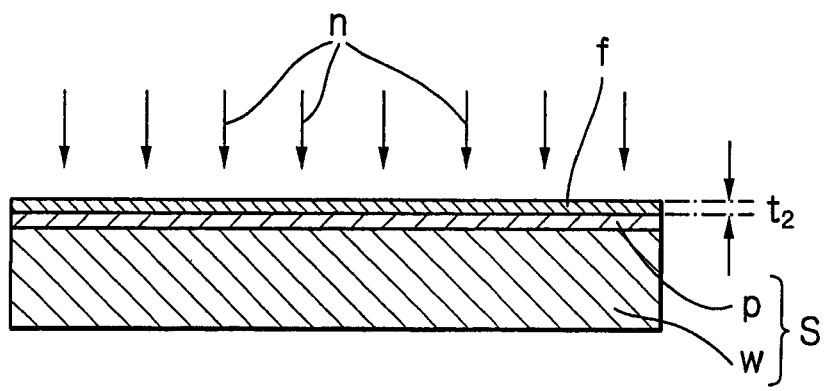

Therefore, in the present invention, as shown in FIG. 4C, a solvent (pure water or ultrapure water n in this embodiment) for the resistive film f is uniformly sprayed over an upper surface of the resistive film f having the thickness $t_1$ formed by the spin coater, to thereby dissolve an upper-side portion of the resistive film f so that the remaining resistive film has a uniform thickness $t_2$. After the film thickness $t_2$ is obtained, by using an inspection mechanism described later and a method known in the art, a primary electron beam, which is a type of a charged particle beam, is emitted to the surface of the wafer W as the sample S, on which the pattern p is formed. A secondary electron beam is emitted from the wafer W and acquired for inspection and evaluation.

Figure 5:
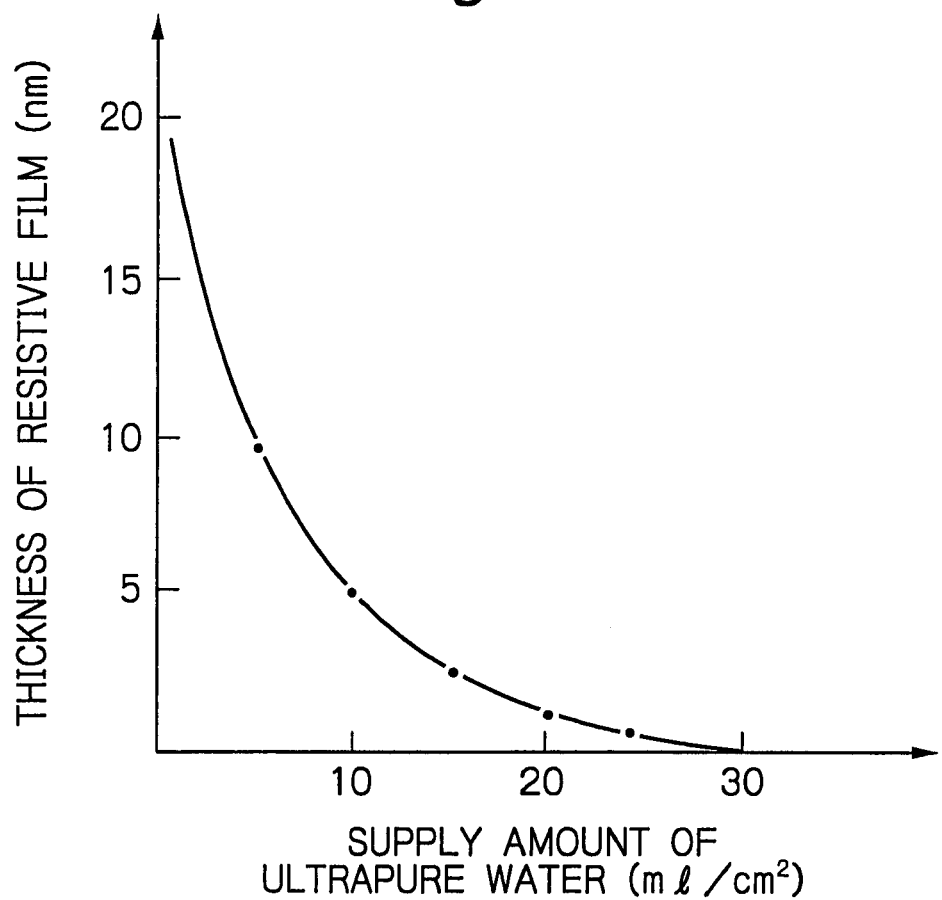
FIG. 5 is a graph indicating the relationship between the thickness of the resistive film remaining on the wafer and the supply amount of ultrapure water when the resistive film coated on the wafer is dissolved in ultrapure water.

Experiments were conducted, in which a resistive film was formed on a wafer by a spin coater (the thickness of the resistive film at this time was 20 nm), and then ultrapure water is sprayed to thereby dissolve the resistive film. As a result, the relationship between the thickness of the resistive film remaining on the wafer and the supply amount of ultrapure water, such as that shown in FIG. 5, was obtained. From FIG. 5, it is apparent that a final thickness of the resistive film can be controlled by appropriately controlling the supply amount of a solvent for dissolving the resistive film, such as pure water or ultrapure water.

Figure 6:
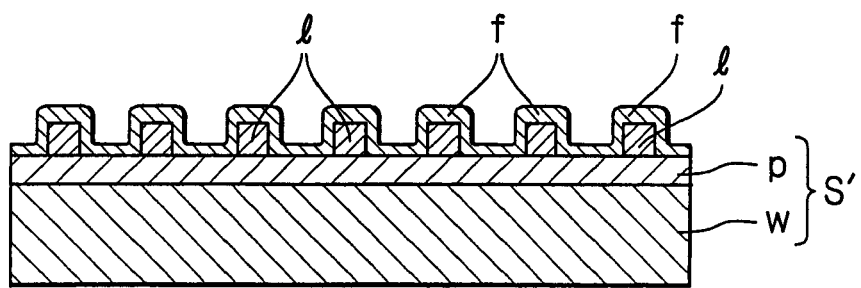
FIG. 6 is an exaggerated cross-sectional view showing an example in which a stepped pattern is formed on a silicon wafer.

FIG. 6 shows a sample S' on which steps are formed on a surface of a layer of pattern p (which steps are formed by a plurality of lines l). In this embodiment also, coating of a resistive film and control of a film thickness can be conducted by the same method as explained above in connection with FIG. 3. In this embodiment, the lines l are spaced equidistant from each other. In the case where distances between the lines l are substantially different, surface electrification becomes different, depending on the distance between the lines l. However, a method of the present invention of forming a thin resistive film having a uniform thickness is effective in obtaining a uniform surface potential.

The water solubility varies according to a type of a resistive film to be applied, a molecular structure thereof, a type of an addition agent, a concentration of a solution and the like. FIG. 7 is a graph representing a relationship between a thickness of a film and a supply amount of pure water, observed under a condition different to that employed in FIG. 5.

In an embodiment of a resistive film forming process, a resistive film solution of a polymer compound of a thienyl alkane sulphonate or isothianaphthenediyl-sulphonate can be employed to form a resistive film. The relationship shown in FIG. 7 represents a film thickness feature in a case that a polymer compound of isothianaphthenediyl-sulphonate and surfactant is utilized as a resistive film solution, the a sample is placed in a spin coater and a resistive film solution is dropped on the sample. Next, the sample is coated with a resistive film, on the spin coater at a rotational speed of, for example, 5000-7000 rpm. Thereby, a resistive film having a thickness of approx. 20 nm is formed. In dissolving the thus formed resistive film, the sample is placed in the spin coater and pure water is dropped on the sample while rotating the spin coater. A rotational speed of the coater is 5000-10,000 rpm. The resistive film is dissolved with pure water or ultra-pure water. FIG. 7 shows a thickness of the resistive film remaining on the sample after dissolution. As is clear from the graph, a thickness of a resistive film can be controlled by adjusting the amount of pure water or ultrapure water to be supplied to dissolve the resistive film.

In conducting an inspection to detect wafer defects, at first a resistive film is formed on the wafer by a process similarly to the above-described embodiment of a resistive film forming process. For example, a Si wafer on which an LSI device structure has been formed is prepared and a resistive film of a polymer compound of isothianaphthenediyle-sulphonate is deposited to be 1 nm in thickness on the Si wafer. Since a thickness of the resistive film formed on the wafer is controllable by the above-mentioned process, a clear electron image with suppressed charge-up, small distortion and minor contrast deterioration can be obtained. Since a contrast of an electron image varies according to a material and structure of a surface, an even clearer electron image having minimum distortion can be obtained by controlling for a resistive film to have an appropriate thickness.

Further, a resistive film forming process can be executed on a photo mask and/or reticle mask.

Figure 8A:
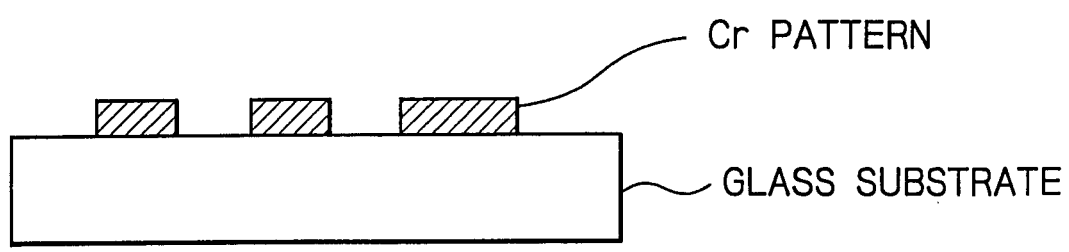
FIGS. 8(A) and 8(B) are exaggerated cross-sectional views showing an example in which a stepped pattern is formed on a silicon wafer.
Figure 8B:
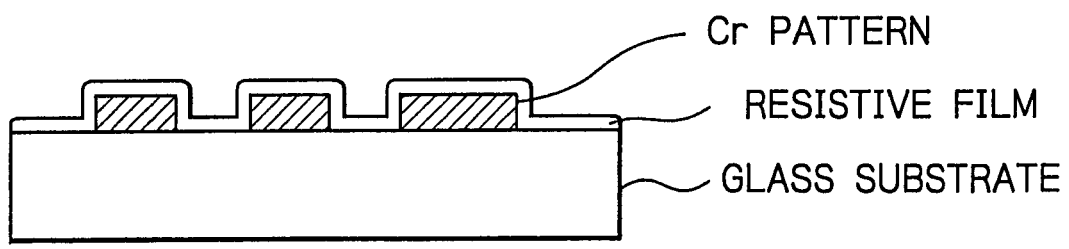

FIGS. 8(A) and 8(B) illustrate cross-sectional views of a photo mask and the same with a resistive film coated thereon. A material of a base structure of the photo mask is silicon glass or quartz glass having a thickness of 1 mm and a material of a pattern is Cr, as shown in FIG. 8(A). A size of the mask is 8×8 inches, a size of a portion of a pattern being 20×20 mm and a size of a minimum pattern being approximately 0.5-0.3 µm. The Cr pattern formed on the substrate has a thickness of 0.1 µm. A resistive film is applied to the surface of the mask by means of spin coating to have a film thickness of 20 nm. Subsequently, the film is dissolved with ultra pure water to have a thickness of 5 nm.

Next, an inspection to detect defects such as pattern defects on the photo mask with the resistive film is conducted by using a scanning electron microscope. Instead of using a scanning electron microscope, an mapping projection method may be employed to conduct an inspection to detect a defect by an electron beam.

If any defect is not found in the inspection, the resistive film is removed by cleaning with ultrapure water in a cleaning mechanism. After the resistive film is removed, the mask can be used as a proper photo mask again for an exposure system.

Although the above example employs a photo mask, the same processing as set forth above may be performed on a reticle mask. In the case of a reticle mask, a pattern reduction rate would be ½-⅕ and a transferred minimum line width would be approximately 0.1-0.5 µm.

In a photo mask or reticle mask, a thin film pattern of metal such as Cr and the like is generally deposited on a surface of a glass material. Since a base material is an insulation glass material such as silicon glass, quartz glass and the like, the surface is allowed to charge-up heavily when an electron beam is applied, which makes it difficult to conduct inspection using an electron beam.

In the present invention, a photo mask or reticle mask is coated with a resistive film to thereby stabilize the potential on the surface of the mask. Thus, even though an electron beam is applied to the mask, charge-up of the mask is obviated and inspection by means of irradiation of an electron beam becomes possible. This is applicable to a scanning electron microscope, projection electron microscope, an inspection apparatus employing an electron beam and the like.

In the resistive film forming method according to the present invention, the thickness of a resistive film on a sample can be precisely controlled so that a resistive film having a desired thickness can be formed uniformly with respect to each sample. Therefore, it is possible to precisely control the amount of electric charge generated by emission of a beam, such as an electron beam or an ion beam, so that a clear potential-contrast image having minimum distortion can be obtained. Conventionally, the thickness of a resistive film cannot be reduced to a level lower than 20 nm. However, a resistive film having a thickness of 0.1 to 1 nm can be obtained in the present invention. Thus, the electric charge on a sample substrate can be appropriately controlled, so that an electron image which is most satisfactory in terms of a potential contrast and distortion can be obtained.

When an electron beam or an ion beam is emitted to a sample substrate, in the case where the beam has an energy as high as about 2 keV or more, there is a possibility of the substrate or device circuits formed thereon being damaged. This possibility can be reduced by effecting observation or inspection according to the present invention. With a high beam energy that will cause device damage in conventional techniques, such damage does not occur and an electron image having minimum distortion can be obtained in the present invention.

In the above resistive film forming process, the desired level of the thickness of the resistive film may be 0.1 nm to 10 nm. The resistive film may be water-soluble. In this case, after inspection of the sample surface, the resistive film may be removed by cleaning with pure water or ultrapure water.

Figure 9:
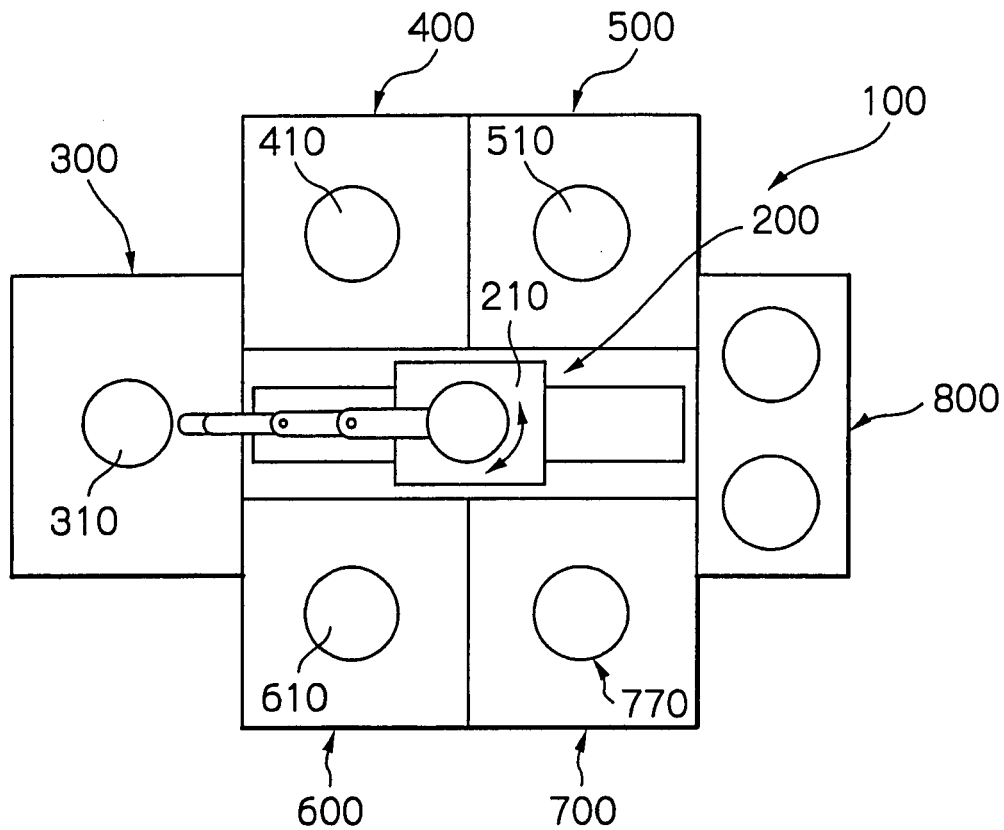
FIG. 9 is a schematic plan view showing disposition of mechanisms forming a surface inspection system for carrying out a surface inspection method according to the invention.

FIG. 9 is a general plan view of an embodiment of a surface inspection system for carrying out a surface inspection method of the present invention. A surface inspection system 100 in this embodiment comprises a central conveyor mechanism 200, and a flattening mechanism 300, a cleaning mechanism 400, a drying mechanism 500, a resistive film coating mechanism 600, an inspection mechanism 700 and a wafer stock interface 800 surrounding the conveyor mechanism 200.

Figure 10:
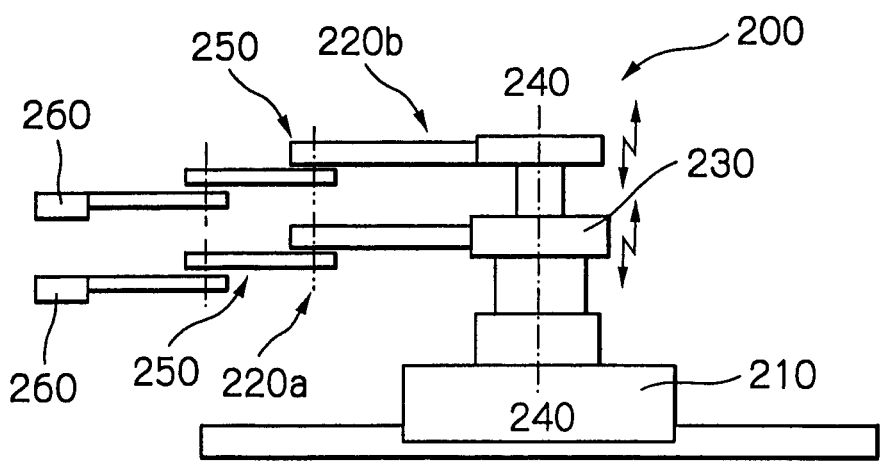
FIG. 10 is a schematic explanatory view of a conveyor robot of a conveyor mechanism applicable to the surface inspection system as shown in FIG. 9.

As shown in FIG. 10, the conveyor mechanism 200 comprises a movable table 210 movable horizontally (in a lateral direction in FIG. 10) and a plurality of (two in this embodiment) articulated conveyor robots 220a and 220b attached to the movable table 210. The conveyor robots 220a and 220b may have the same structure which is known in the art. Each conveyor robot comprises a base 230, an articulated arm 250 and a chuck 260. The base 230 is vertically movable relative to the movable table 210 and pivotable about an axis 240-240. The articulated arm 250 is connected to the base 230. The chuck 260 is connected to a forward end arm of the articulated arm 250 so as to hold a wafer W. The articulated arm 250 may have a known structure which comprises a plurality of (three in this embodiment) arm members connected so as to be pivotally movable relative to each other. The chuck 260 also may have a known structure. Therefore, detailed description of structures and operations of the articulated arm 250 and the chuck 260 is omitted. The conveyor mechanism 200 conveys a wafer between the above mechanisms 300, 400, 500, 600 and 700, and between each mechanism and the wafer stock interface 800. A wafer held by the chuck 260 of the conveyor robot 220a or 220b is directly loaded on a work station of each mechanism, that is, a stage device, and a wafer is unloaded from the stage device directly by the conveyor robot 220a or 220b. Therefore, differing from conventional independent apparatuses which conduct the same operations as the above-mentioned mechanisms, a loading/unloading robot for each mechanism can be eliminated. Further, in the conveyor mechanism 200 in this embodiment in which a plurality of conveyor robots 220a and 220b are provided, when a wafer is loaded on or unloaded from, for example, the coating mechanism 600, a new wafer held by one conveyor robot 220a is moved to a position close to the coating mechanism 600, and a wafer after coating is removed from the coating mechanism 600 by the other conveyor robot 220b, and the new wafer held by the conveyor robot 220a is placed on a stage device of the coating mechanism 600. Thus, a wafer is loaded on or unloaded from a stage device of each mechanism directly by the conveyor mechanism 200. Therefore, the loading/unloading robots for the respective mechanisms can be eliminated, thus eliminating operations of these robots and simplifying a conveying process.

A basic arrangement of the flattening mechanism 300 may be the same as those of a CMP apparatus having a known structure, a reactive ion flattening apparatus using plasma, etc. Therefore, detailed description of a structure and an operation of the flattening mechanism 300 is omitted. The flattening mechanism 300 differs from a conventional independent flattening apparatus such as a conventional CMP apparatus in that a wafer is loaded on a work station, namely, a stage device 310, directly by means of the conveyor robot 220a or 220b of the conveyor mechanism 200, and that a wafer loading station and a loading/unloading robot for conveying a wafer between the conveyor mechanism 200 and the stage device 310 are not provided.

A basic arrangement of the cleaning mechanism 400 may be the same as that of a conventional cleaning apparatus adapted to clean a wafer using pure water or ultrapure water, except that a loading/unloading robot and a wafer loading station are eliminated. Therefore, detailed description of a structure and an operation of the cleaning mechanism 400 is omitted. A wafer is loaded on a stage device 410 directly by the conveyor mechanism 200. The drying mechanism 500 may be a conventional drying apparatus of a type which blows dry air or a nitrogen gas against a wafer, a vacuum drying type or a heat-drying type. Therefore, detailed description of a structure and an operation of the drying mechanism 500 is omitted. The drying mechanism 500 differs from a conventional independent drying apparatus in that a wafer is loaded on a stage device 510 directly by the conveyor robot 220a or 220b of the conveyor mechanism 200, and that a wafer loading station and a loading/unloading robot for conveying a wafer between the conveyor mechanism 200 and the stage device 510 is not provided.

The resistive film coating mechanism 600 comprises a conventional coating apparatus, such as a spin coater, and a film thickness uniformalizing mechanism 650 for dissolving a part of a resistive film to thereby reduce and uniformalize the thickness of the resistive film. Therefore, in the resistive film coating mechanism 600, a mechanism for coating a resistive film is the same as that of a conventional spin coater and is therefore not described in detail. Only a basic arrangement of the film thickness uniformalizing mechanism 650 is explained, with reference to FIG. 11.

Figure 11:
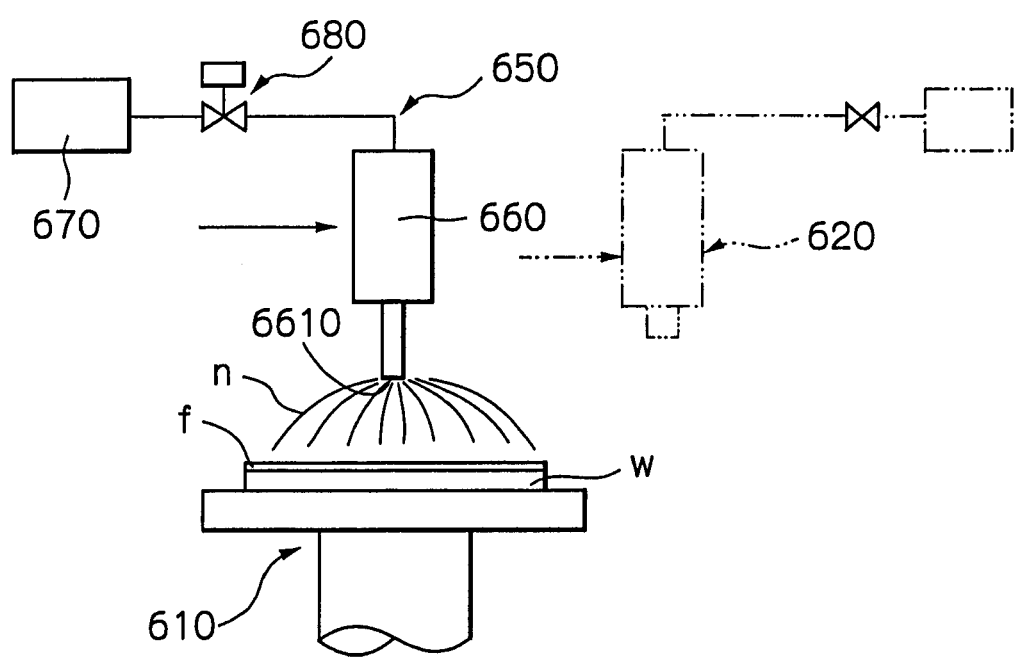
FIG. 11 is a schematic side view for explaining an example of a film thickness uniformalizing mechanism applicable to the system as shown in FIG. 9.

Referring to FIG. 11, the film thickness uniformalizing mechanism 650 comprises a micro syringe 660 movable to a position above a rotor 610 of the resistive film coating mechanism 600. The micro syringe 660 is connected through a control valve 680 and a flexible pipe to a supply source 670 of pure water or ultrapure water. In the film thickness uniformalizing mechanism 650, a wafer W is held on the rotor 610 of a spin coater under force of vacuum, and a resistive film material in liquid form is sprayed from a film material dropping head 620 over the wafer W, to thereby conduct coating. At this time, a resistive film having a thickness $t_1$ is formed on the wafer W. Thereafter, the film material dropping head 620 is moved away from the position above the rotor 610, and the micro syringe 660 is moved to that position, in place of the film material dropping head 620. Then, while the wafer W is rotated at a rate of, for example, 3,000 rpm to 7,000 rpm by the rotor 61, pure water or ultrapure water n from the supply source 670 is jet-sprayed or shower-sprayed through a spray opening 6610 of the micro syringe 660 uniformly over an upper surface of the resistive film f coated on the wafer W. Because the resistive film f is water-soluble, an upper-side portion of the resistive film which makes contact with pure water or ultrapure water is dissolved. The thickness $t_2$ of the resistive film to be left on the wafer W is controlled by determining the supply amount of pure water or ultrapure water in consideration of the surface area of the wafer W and the initial film thickness $t_1$. The thickness $t_1$ of the resistive film at the time of completion of coating by a spin coater can be made 20 nm, which is a lower limit of a film thickness obtained by using a conventional spin coater. However, the thickness $t_1$ may be larger than 20 nm. The thickness $t_2$ of the resistive film f remaining on the wafer W after dissolution of a part of the resistive film f in a solvent, such as pure water or ultrapure water, is preferably 0.1 nm to 10 nm. When the film thickness $t_2$ is smaller than 0.1 nm, an effect of suppressing charge-up cannot be obtained, thus preventing high-precision observation. When the thickness $t_2$ is larger than 10 nm, the number of detected electrons (such as secondary electrons) emitted from the resistive film f itself increases, and electrons (such as secondary electrons) emitted from the surface of a sample (such as a wafer) underneath the resistive film are scattered within the resistive film, thus generating a change in an electron orbit and deterioration of an acquisition value (a blur). The thickness $t_2$ of the resistive film f is more preferably 0.5 nm to 2 nm.

Figure 12A:
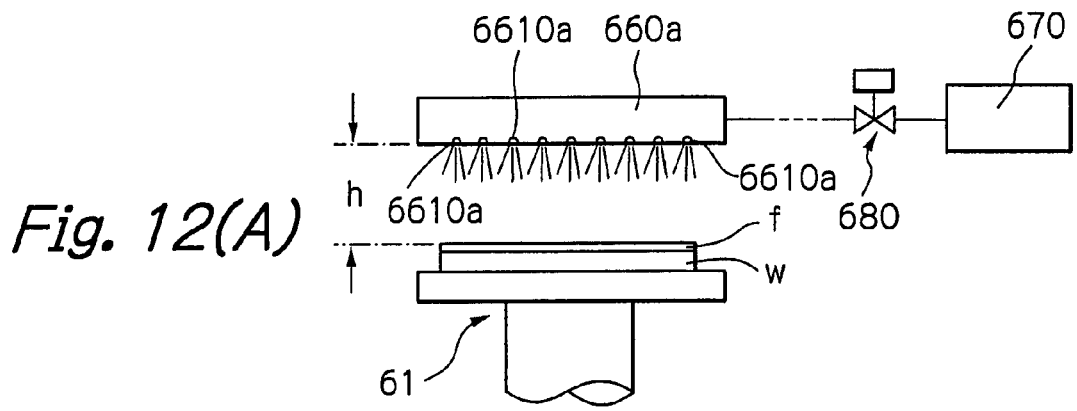
FIGS. 12(A)-12(D) are schematic side views for explaining other examples of film thickness uniformalizing mechanisms applicable to the system shown in FIG. 9.
Figure 12B:
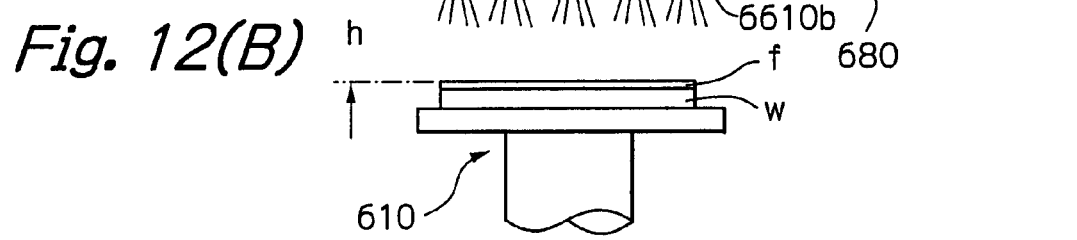
Figure 12C:
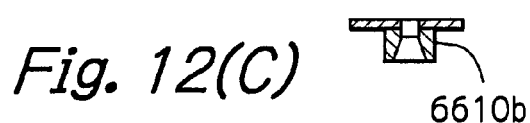
Figure 12D:
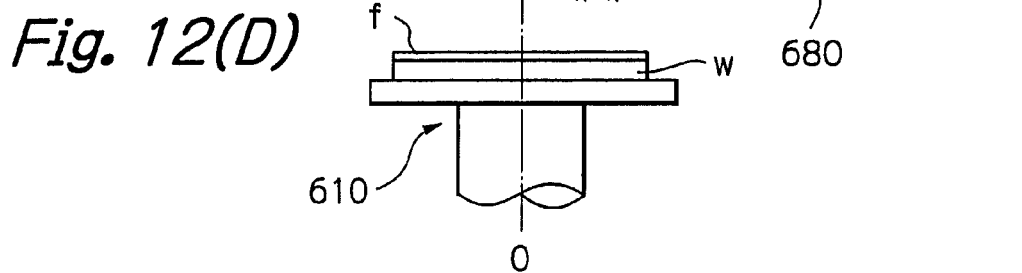

FIG. 12(A) shows another example of a film thickness uniformalizing mechanism. In this example, while a wafer W is placed on the rotor 610 and rotated (at a rate of, for example, 1,000 to 10,000 rpm), a supply head 660a is disposed at a position above the wafer W (at a height h from the wafer W). The supply head 66a extends along a diameter passing through the axis of rotation of the rotor 610. The supply head 66a includes a number of flow apertures 6610a formed in a lower surface thereof, which are arranged at predetermined spaced intervals in a longitudinal direction of the supply head 660a. Pure water or ultrapure water flows from the flow apertures 6610a, to thereby dissolve a part of the resistive film f in pure water or ultrapure water. In this case, the thickness $t_2$ can be controlled by controlling a total amount of pure water or ultrapure water supplied from the supply head 66a through the flow apertures 661a, by means of the control valve 680. Instead of the supply head 66a having the flow apertures 6610a, a supply head 660b as shown in FIG. 12(B) may be used. The supply head 660b includes a plurality of (five in this example) nozzles 6610b formed on a lower surface thereof, each having a cross-section such as that shown in FIG. 12(C). In this case, pure water or ultrapure water is jet-sprayed from the nozzles 661b. In either case, the distance h between the flow apertures 6610a or the nozzles 6610b and the surface of the resistive film f on the wafer W should be appropriately selected so that pure water or ultrapure water can be sprayed uniformly all over the upper surface of the resistive film f. FIG. 12(D) shows a further example of a film thickness uniformalizing mechanism. In this example, while a wafer W is rotated by the rotor 610, a supply head 660c is moved reciprocally or in one direction between an axis O-O of rotation of the rotor 610 and a position at an outer periphery of the rotor 610, along a diameter passing through the axis O-O of rotation of the rotor 610. Thus, pure water or ultrapure water is sprayed from nozzles 6610*c* of the supply head 660*c*, to thereby dissolve the resistive film f.

Figure 13:
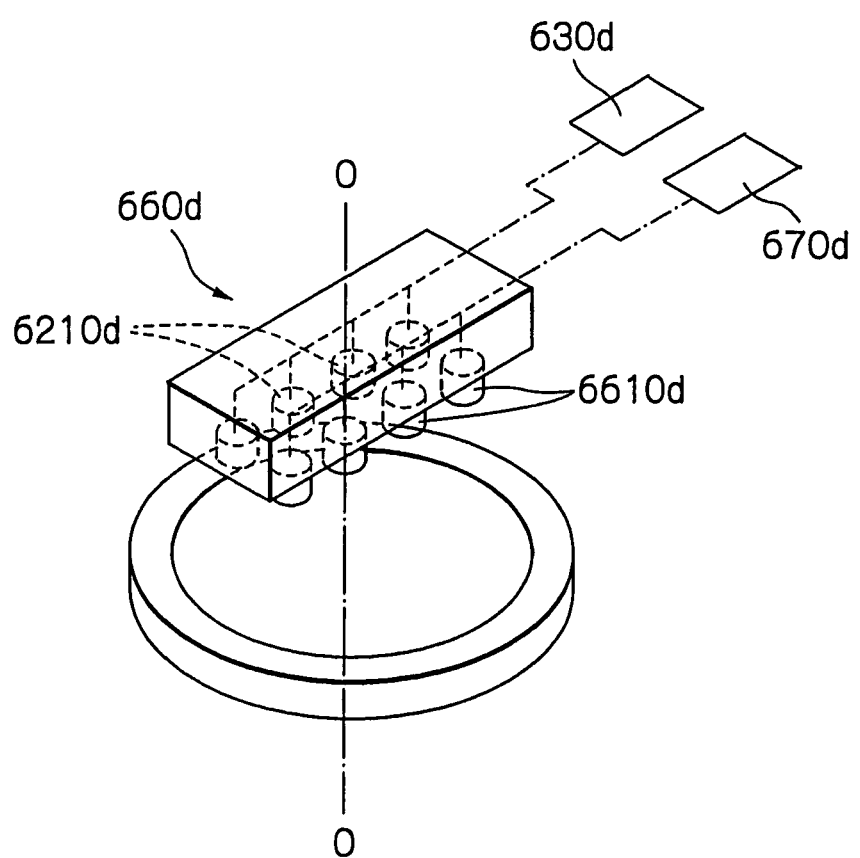
FIG. 13 is a schematic perspective view for explaining a further example of a film thickness uniformalizing mechanism applicable to the system shown in FIG. 9.

FIG. 13 shows a still further example of a film thickness uniformalizing mechanism. In this example, a supply head 660*d* is disposed above the rotor 610. The supply head 660*d* includes a plurality of nozzles 6210*d* for spraying a film material in liquid form over a wafer and a plurality of nozzles 6610*d* for spraying a solvent such as pure water or ultrapure water over a resistive film. The nozzles 6210*d* are connected to a supply source 630*d* of a film material in liquid form, and the nozzles 6610*d* are connected to a supply source 670*d* of a solvent. With this arrangement, it is unnecessary to move the supply head for coating a resistive film or for supplying a solvent.

The thickness $t_2$ of the resistive film remaining on the wafer after dissolution of an upper-side portion of the resistive film is measured by an optical measurement method using an ellipsometer, or a method using a step height measurement device, such as a surface roughness measurement device or an atomic force microscope. If desired, measurement of a film thickness can be conducted more precisely by using Auger spectroscopy, SIMS, or characteristic X-ray analysis measurement.

Measurement of a film thickness may be conducted with respect to each wafer, although a cumbersome operation is required and a throughput lowers. Normally, suitable conditions are preliminarily determined by conducting experiments so as to obtain the relationship between the film thickness $t_2$ (obtained after dissolution of a part of a resistive film) and various conditions, such as the supply amount of pure water or ultrapure water, the rotation speed of a wafer and the film thickness $t_1$ prior to dissolution. Uniformalization of the film thickness is conducted based on this relationship, and reproducibility in the film thickness due to variation in the conditions is examined by sampling. Therefore, the surface inspection system in this embodiment does not include a device for measurement of a film thickness.

After uniformalization of the film thickness, the wafer is introduced into the inspection mechanism (or surface inspection apparatus) 700. As to the inspection mechanism 700, embodiments thereof will be explained later.

The wafer stock interface 800 (in FIG. 9) includes a plurality of (at least two) cartridges, each accommodating a plurality of wafers arranged vertically in a spaced relationship. A wafer can be removed from the cartridge by means of the conveyor robot 220*a* or 220*b* of the conveyor mechanism 200. This arrangement is known in the art. Therefore, detailed description of the wafer stock interface 800 is omitted.

By providing the components of the surface inspection system 100 (i.e., the central conveyor mechanism 200, the flattening mechanism 300, the cleaning mechanism 400, the drying mechanism 500, the resistive film coating mechanism 600, the inspection mechanism 700 and the wafer stock interface 800) in one large chamber, and maintaining the inside of the chamber in a vacuum or an inert gas atmosphere, contamination of wafers during conveyance can be prevented.

Using the surface inspection system 100 as illustrated in FIG. 9, a wafer is processed in the following sequence of steps.

1) Pre-Processing: a wafer is pre-processed.
2) Wafer Conveyance: after pre-processing, the wafer is supplied to a wafer station 810 of the wafer stock interface 800.
3) Wafer Loading: the wafer is loaded on the conveyor robot 220*a* or 220*b* of the conveyor mechanism 200.
4) Wafer Cleaning: the wafer is conveyed to the cleaning mechanism 400 by the conveyor robot 220*a* or 220*b*, and cleaned.
5) Flattening: the wafer is conveyed to the flattening mechanism 300 by the conveyor robot 220*a* or 220*b*, and flattened.
6) Cleaning: the wafer is conveyed to the cleaning mechanism 400 by the conveyor robot 220*a* or 220*b*, and cleaned.
7) Drying: the wafer is conveyed to the drying mechanism 500 by the conveyor robot 220*a* or 220*b*, and dried.
8) Resistive Film Coating and Film Thickness Control: the wafer is conveyed to the resistive film coating mechanism 600 by the conveyor robot 220*a* or 220*b*, and coated with a resistive film having a desired thickness $t_1$.
9) Inspection: the wafer is conveyed to the inspection mechanism 700 by the conveyor robot 220*a* or 220*b*, and an electron beam or electromagnetic wave beam is emitted to the wafer for inspection.
10) Cleaning: the wafer is conveyed to the cleaning mechanism 400 by the conveyor robot 220*a* or 220*b*, and the resistive film on the wafer is completely removed.
11) Drying: the wafer after cleaning is conveyed to the drying mechanism 500 by the conveyor robot 220*a* or 220*b*, and dried.
12) Wafer Unloading: the wafer is conveyed to a wafer station 820 of the wafer stock interface 800 by the conveyor robot 220*a* or 220*b*.
13) Wafer Conveyance: the wafer is conveyed to a post-process.
14) Post-Processing: the wafer is post-processed.

A plurality of wafers can be processed at the same time in the above operating sequence, using the surface inspection system of the present invention. For example, while one wafer is being flattened, another wafer can be coated with a resistive film and inspected. Thus, it is possible to reduce the time required for processing wafers for device manufacturing. Therefore, processing time for each sample can be reduced and a defect in each process can be early detected.

The surface inspection system illustrated in FIG. 9 may be additionally provided with a repairing mechanism, a pattern forming mechanism, a developing mechanism, a resin film coating mechanism and the like. In this way, it is possible to flatten, form patterns, evaluate pattern forming masks for defects, and repair defective masks.

Embodiments of the inspection mechanism 700 will next be explained with reference to FIGS. 14-20. It should be noted that these embodiments can be employed dependently and independently on the system shown in FIG. 9.

Figure 14:
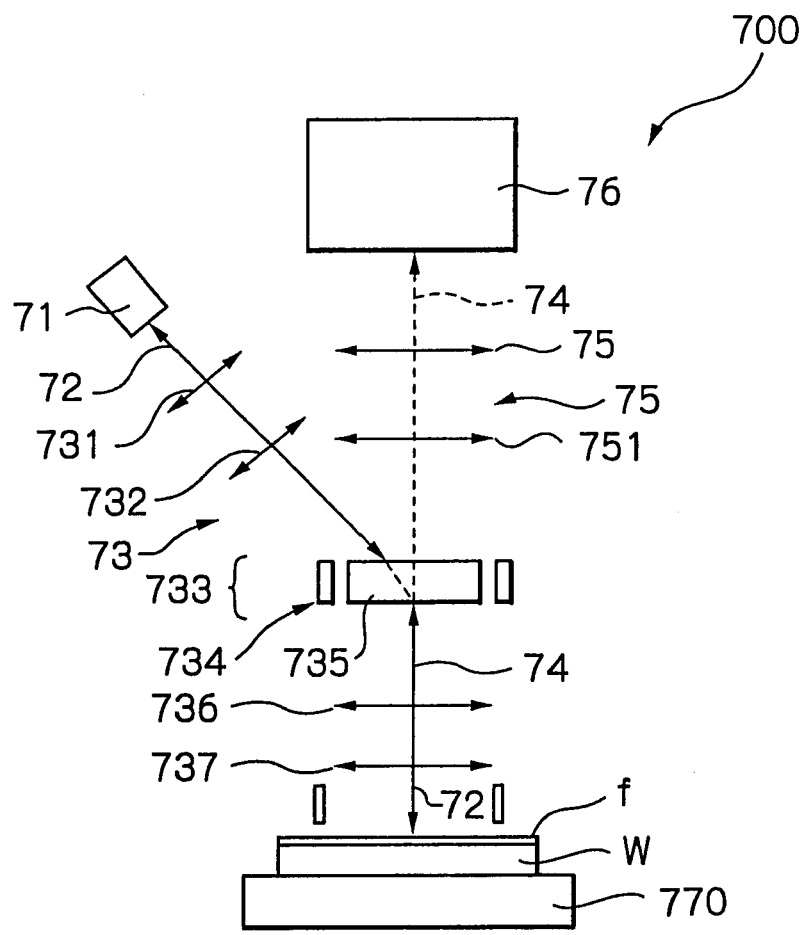
FIG. 14 is a diagram showing a general construction of a first embodiment of a surface inspection apparatus (or mechanism) applicable to the system shown in FIG. 9.

FIG. 14 shows a first embodiment of the inspection mechanism 700, which is an electron beam apparatus. The electron beam apparatus 700 shown in FIG. 14 is an imaging projection type electron beam apparatus which comprises an electron gun 71 for emitting a primary electron beam (a shaped beam) 72 shaped by a square opening, a primary electron optical system (hereinafter, referred to simply as "the primary optical system") 73 for emitting the primary electron beam 72 to a wafer W, a secondary electron optical system (hereinafter, referred to simply as "the secondary optical system") 75 for acquiring secondary electrons 74 emitted from the wafer W by the irradiation of the primary electron beam 72, and a detector 76 for detecting the secondary electrons 74. In this electron beam apparatus 700, the primary electron beam 72 emitted from the electron gun 71 is reduced by two lens systems 731 and 732 of the primary optical system 73, and an image is formed in a size of 1.25 square mm at a center plane of an ExB separator 733. The electron beam deflected by the ExB separator 733 is reduced to ⅕ by lenses 736 and 737, and projected on the wafer W. The secondary electrons 74 having pattern image data emitted from the wafer W pass through the lenses 736 and 737. The secondary electron beam is then magnified by magnification lenses 751 and 752 of the secondary optical system 75, and forms a secondary electron image at the detector 76. In this electron beam apparatus, the ExB separator 733 is adapted to deflect the primary electron beam 72 emitted from the electron gun 71, while allowing the secondary electrons 74 from the surface of the sample to pass straightforward through the ExB separator 733, and the primary electron beam 720 to become incident at a right angle on the surface of the sample.

Of the four magnification lenses 736, 737, 751 and 752, the lenses 736 and 737 form a symmetrical doublet, and the magnification lenses 751 and 752 also form a symmetrical doublet, thus providing a lens system having no distortion. However, slight distortion will be generated due to contamination of electrodes. Therefore, periodically, a reference pattern is placed at the sample plane, and measurement of distortion is conducted to calculate a parameter for correction of distortion.

When inspection is conducted by the imaging projection type electron beam apparatus shown in FIG. 14, with respect to a wafer on which an oxide film or a nitride film is selectively formed, the problem of distortion cannot be effectively avoided by only correcting distortion of an optical system. After acquisition of image data, selected points on a pattern edge are compared with a data image, to thereby correct distortion. Thereafter, comparison is made between dies (or chips), or between image data and a data image, to thereby detect a defect.

In the inspection mechanism 700 comprising an electron beam apparatus in this embodiment, a conveyor robot for conveying a wafer from the conveyor mechanism 200 to a stage 770 of the electron beam apparatus of the inspection mechanism 700 is not provided.

Figure 15:
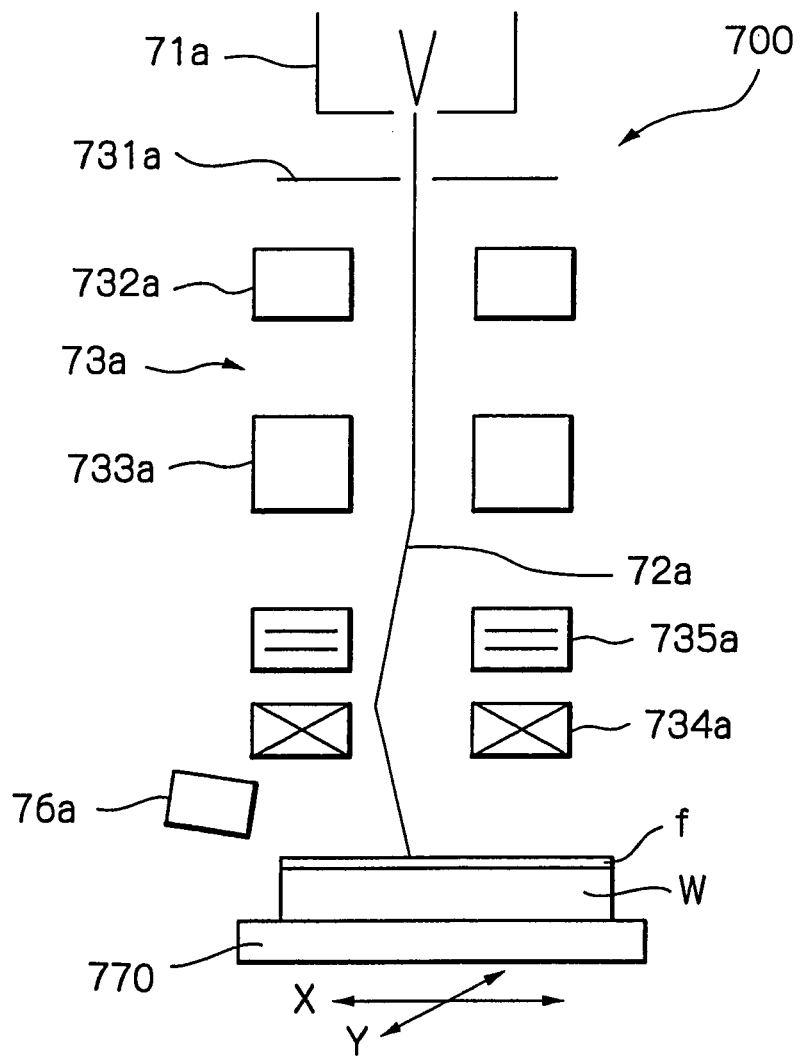
FIG. 15 is a diagram showing a general construction of a second embodiment of a surface inspection apparatus (or mechanism) applicable to the system shown in FIG. 9.

FIG. 15 shows a second embodiment of a sample surface inspection apparatus or mechanism 700. The inspection apparatus in this example comprises a scanning type electron beam apparatus. This scanning type electron beam apparatus 700 comprises an electron gun 71a for emitting a primary electron beam, a primary electron optical system (hereinafter, referred to simply as "the primary optical system") 73a for illuminating a wafer W with the primary electron beam which has been emitted from the electron gun 71a and shaped, and a detector 76a for detecting electrons, such as secondary electrons, emitted from the wafer W. In this electron beam apparatus, primary electrons emitted from the electron gun 71a are accelerated by anode, and pass through an aperture formed by an aperture plate 731a of the primary optical system 73a, to thereby form an electron beam 72a, which in turn passes through lens systems 732a and 733a and illuminates the wafer W on which the resistive film f is formed. A scanning operation and magnification of the primary electron beam 72a are controlled by a scanning coil 734a and a lens system 735a. Secondary electrons, backscattered electrons or reflected electrons emitted as a result of irradiation of the primary electron beam 72a are detected by the detector 76a, such as a photomal, and form a secondary electron image. The wafer W is attached to a movable stage 770, and continuously moved in an X- or Y-direction at a rate corresponding to an image magnification. Thus, a continuous image can be obtained, by using a liner sensor. Using this secondary electron image, comparison is made between dies (or chips) or between image data and a data image, thus detecting a defect in the wafer W.

FIGS. 16-20 respectively show third through seventh embodiments of an inspection mechanism 700. In FIGS. 16-20, the same reference numerals denote the same or similar components.

First, the concept of these embodiments of the apparatus will be described below.

Each of these embodiments is characterized in that an electromagnetic wave is irradiated onto a surface of a sample, photoelectrons generated thereby is detected, and an image is formed on the basis of the electrons. Particularly, electromagnetic waves having wavelengths of 400 nm or less such as ultraviolet rays, X-rays and the like, are suitable to utilized in the invention. Such electromagnetic waves can limit the amount of charge on the sample surface, so that less distorted images can be obtained. Also, the electromagnetic wave can be uniformly irradiated even when a potential distribution occurs on the sample surface. It is therefore possible to acquire a uniform and clear potential contrast image in the field of view.

Also, since the electromagnetic waves are consistent in irradiation characteristic irrespective of the properties of materials irradiated therewith, they can be irradiated to any material. For example, the electromagnetic waves can be similarly irradiated to such samples as semiconductor, LSI, metal, insulating material, glass, living material, polymer material, ceramic, or a composite material thereof, to evaluate the sample surface.

The surface inspection apparatus comprises an electron beam generator together with an electromagnetic wave generator, so that they can be selectively driven for irradiation or simultaneously driven for irradiation. For example, for evaluating a surface of a semiconductor waver on which a variety of circuit configurations are formed over multiple layers, an electromagnetic wave can be irradiated to a circuit and a layered structure which must be protected from damages, while an electron beam can be irradiated to a circuit and a layered structure which need not be protected from damages.

When damages need not be taken into consideration, a sample can be irradiated with an electron beam having electron irradiation energy selected approximately in a range of 0 to 4 keV to provide best images. For example, when an electron beam having 2-3 keV is irradiated to a wafer having simple L/S metal wires and insulating materials such as $SiO_2$, a less distorted image can be produced than when it is irradiated with an electron beam having lower energy.

When damages must be taken into consideration, the breakdown may be increased for gate oxide films and insulating thin films. In such a case, less distorted accurate images can be produced with less damages by selecting an appropriate electromagnetic wave for irradiation. By the irradiation of electromagnetic wave, photoelectrons are emitted from a surface of a sample. Because of low emission energy, the electrons can more readily achieve a focusing condition by an electro-optical system. For example, in an imaging optical system, it is possible to achieve a resolution of 0.1 μm or less, and a maximum image height of 50 μm or more in the field of view.

As to an imaging optical system, it is composed such that electron beams are irradiated on a field of view or evaluation range of a sample surface to obtain an image of the field of view, enlarging the image by an electro-optical system, and inspecting the sample on the basis of the enlarged image. Namely, a system in which electron beams are irradiated on a field of view extending at least one dimension on a sample (but not only one point) to obtain an image, is generally called a system of "an imaging type".

As described above, the present invention permits a selection from the following three approaches:
(1) Photoelectrons emitted from a sample surface irradiated with an electromagnetic wave such as ultraviolet ray are detected to generate an electron image of the sample surface;
(2) Secondary electrons emitted from a sample surface irradiated with an electron beam are detected to generate an electron image of the sample surface; and
(4) Photoelectrons and secondary electrons emitted from a sample surface irradiate with both an electromagnetic wave such as ultraviolet ray and an electron beam to generate an electron image of the sample surface.

An appropriate approach is selected for use from the foregoing three approaches on the basis of a charging characteristic and anti-damage characteristic associated with a material, structure and the like of a particular sample. In this way, it is possible to efficiently acquire an electron image of a sample surface with high quality while preventing damages on the sample. For example, a semiconductor wafer can be effectively evaluated for detecting defects.

For the electromagnetic wave generator, a lamp light source such as mercury lamp, a deuterium lamp, an excimer lamp, or a laser light source may be used as an ultraviolet ray source. Fourth-order harmonic waves of ArF, KrF excimer laser, Nd:YAG laser may be used as a laser. The ultraviolet ray or laser is guided by a light guide or an optical fiber, such that it can be irradiated onto a surface of a sample placed in a vacuum chamber. Optical lenses may be used to control an irradiated region and an optical density.

Also, a resist film may be coated on a sample surface for preventing the surface from being charged. While the irradiation of an electromagnetic wave does not cause large charging, the resist film may be coated to generate high quality images which are less distorted when an image is distorted even with slight charging, or when small distortions must be corrected for generating a precise image. A resist film may be coated on a sample which is irradiated with an electron beam, in which case a less distorted image can be generated.

With the realization of the foregoing features, it is possible to provide electron emission characteristics more suitable for the properties of particular circuits and layered structures and efficiently generate high quality images while preventing damages and distorted images.

In the example mentioned above, ultraviolet rays, ultraviolet laser, X-rays, X-ray laser may be used as the electromagnetic waves. Alternatively, photoelectrons may be emitted using visible light or the like which has a wavelength longer than ultraviolet rays and X-rays. The latter sources can be applied when a sample has a small work function, when multiple photons are absorbed, and the like.

It is also possible to employ an imaging optical system for detecting electrons emitted from a sample surface in order to improve a throughput for evaluating the sample surface. For example, a detector using MCP/screen/relay lens/CCD structure can be used for acquiring images in multiple portions in a step & repeat system. Alternatively, a detector using MCP/screen/relay lens/TDI structure can be used for sequentially acquiring images.

Since the use of such an imaging optical system allows simultaneous detection of electrons which are two-dimensionally emitted from a sample surface, a two-dimensional electron image can be rapidly acquired. A sample can be evaluated for detecting defects and the like at a high throughput, by utilizing this feature and the aforementioned detector.

Since a sample can be inspected or evaluated at a high throughput in the middle of and after completion of a process using the aforementioned surface inspection apparatus, semiconductor devices can be necessarily manufactured at a high throughput.

A semiconductor device manufacturing system can be built to have a surface inspection apparatus using an electromagnetic wave, or a surface inspection apparatus using both of an electromagnetic wave and an electron beam, and a surface flattening mechanism. For example, the semiconductor device manufacturing system can be formed to associatively arrange a wafer carrying mechanism, a surface inspection mechanism, a surface flattening mechanism, and a sample drying mechanism in such a manner that a dried semiconductor wafer is introduced into the surface processing apparatus and removed therefrom in a dried state.

The system may be additionally provided with a resin film coating mechanism, a pattern forming mechanism, a developing mechanism, and a defect repairing mechanism.

Figure 16:
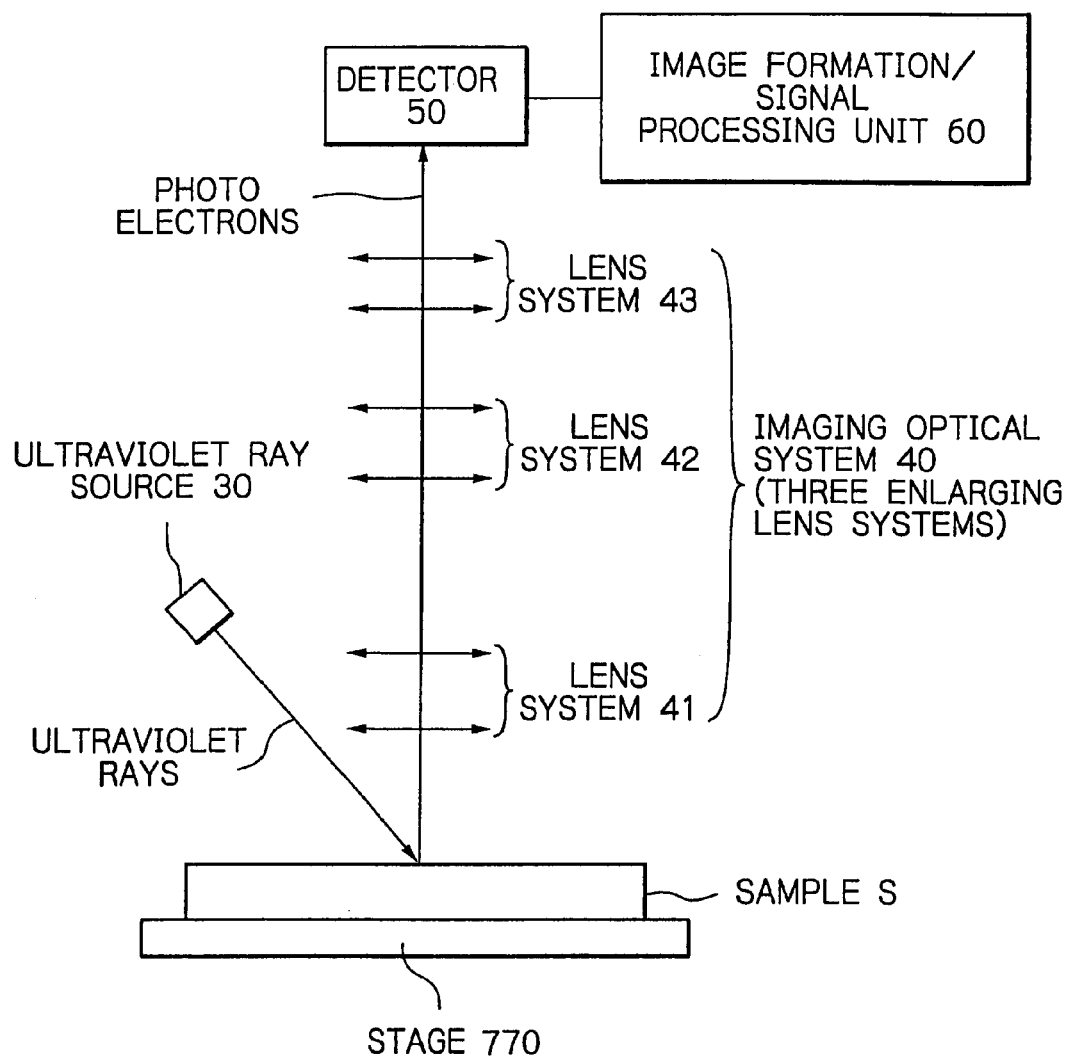
FIG. 16 is a diagram showing a general construction of a third embodiment of a surface inspection apparatus (or mechanism) applicable to the system shown in FIG. 9.

FIG. 16 explanatorily shows a third embodiment of the inspection mechanism or apparatus 700. The inspection apparatus in FIG. 16 comprises a stage 770 on which a sample S is carried; an ultraviolet ray source 30 for generating an electromagnetic wave; an imaging optical system 40 having three enlarging lens systems 41-43; a detector 50 for detecting photoelectrons; and an image formation/signal processing unit 60. Each of the lens systems 41-43 comprises two or more lenses for a high resolution and a high zooming ratio.

The sample S is, for example, a wafer in which circuit patterns are formed on silicon substrates, in the middle of or after completion of a semiconductor device manufacturing process. While the semiconductor device manufacturing process includes a variety of steps, the ultraviolet ray source 30 irradiates ultraviolet rays to the surface of the wafer to emit photoelectrons from the surface of the sample S, which are detected by the detector 50 through the imaging optical system 40. An electric signal or an optical signal output from the detector 50 is processed in the image formation/signal processing unit 60 for evaluating the presence or absence of debris, defective conduction, defective patterns, drops and the like, state determination, classification and the like in all steps which include those in the semiconductor device manufacturing process.

Figure 17:
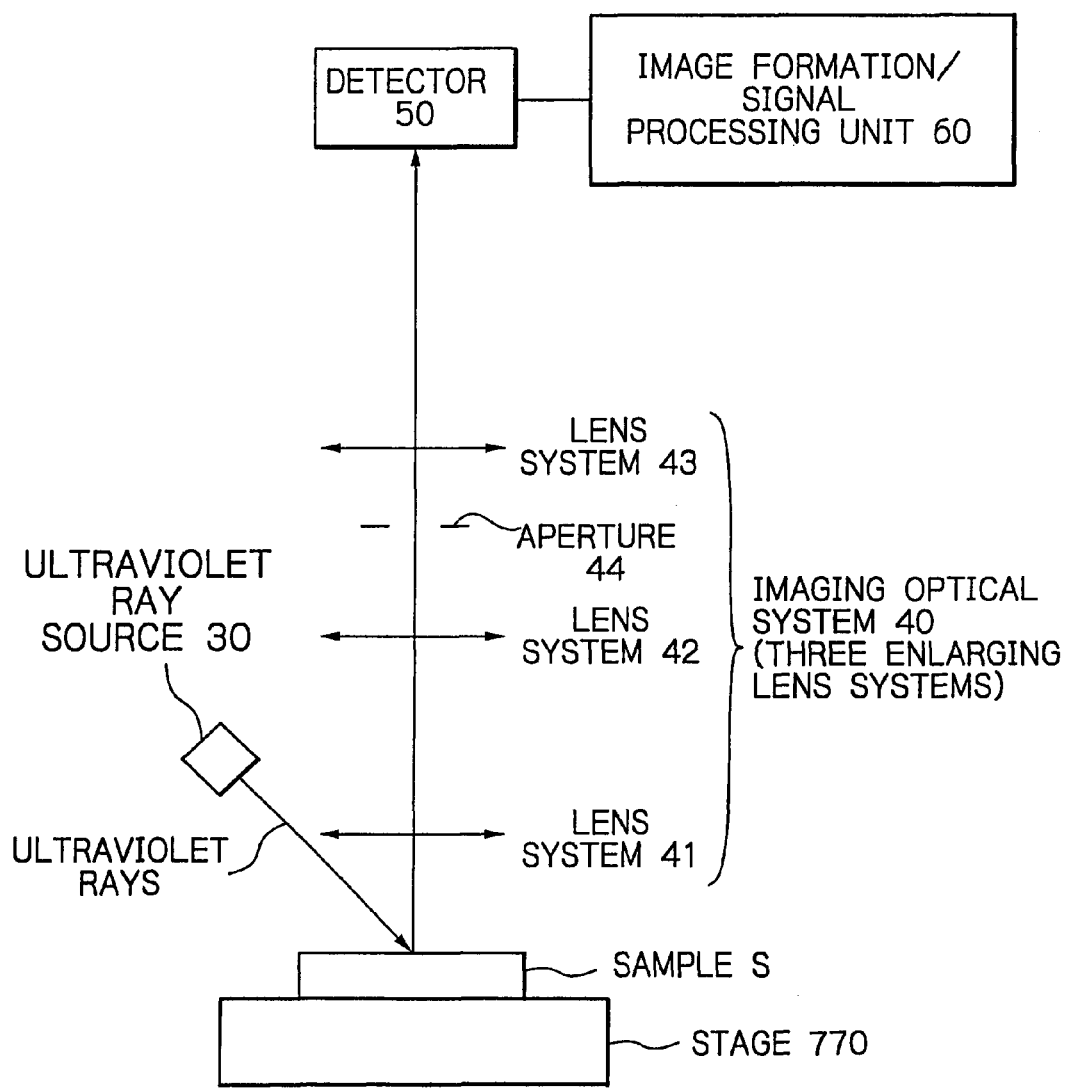
FIG. 17 is a diagram showing a general construction of a fourth embodiment of a surface inspection apparatus applicable (or mechanism) to the system shown in FIG. 9.

FIG. 17 illustrates a fourth embodiment of the inspection mechanism or apparatus 700. The apparatus of the fourth embodiment correspond to the third embodiment shown in FIG. 16, provided that each of the lens systems 41-43 of the third embodiment is replaced with a single lens. In FIG. 17, an aperture plate 44 is disposed between the second lens 42 and the third lens 43 of the imaging optical system 40. The aperture plate 44 is utilized for noise cutting, transmittance control and aberration amount control. Though not shown in FIG. 16, a similar aperture plate is also provided in the third embodiment.

In the fourth embodiment, a sample S is a silicon wafer having a size of 8-12 inches is carried on an X-Y-θ control stage 770. The wafer is formed with circuit patterns of LSI in the middle of manufacturing. A detector 50 used herein can be composed of an electronic amplifier, an opto-electronic converter and a TDI.

An ultraviolet ray source 30 used herein is a mercury lamp which irradiates ultraviolet rays into a vacuum chamber (not shown) by an appropriate light guide (not shown) onto the surface of the sample S. An ultraviolet irradiation region is adjusted by optical lenses or the like (not shown) such that the region has a diameter approximately in a range of 0.01 mm to 10 mm. Photoelectrons are generated from the surface of the wafer by the irradiation of ultraviolet rays. The photoelectrons are guided to the detector 50 by the imaging optical system 40. Since the imaging optical system 40 can provide a focus scaling ratio of approximately 50-500 by the three lenses 41-43, the detector 50 two-dimensionally detects a pattern on the wafer, resulted from a difference in photoelectron generation characteristics (such as a working function) on the wafer surface, and the image formation/signal processing unit 60 forms images and processes signals. Through the signal processing, defects are detected and classified.

Using the detector 50 and stage 770 in synchronism, wafers can be evaluated in sequence. The TDI detector can also detect electron images in sequence while the stage 770 is moved in sequence. The use of this strategy can save a loss time involved in stop/move and loss time until a moving speed is stabilized, as compared with the step & repeat system, thereby efficiently performing evaluations such as detection of defects.

While the third and fourth embodiments have shown examples in which the electromagnetic rays are used as ultraviolet rays, X-rays may be irradiated instead.

Figure 18:
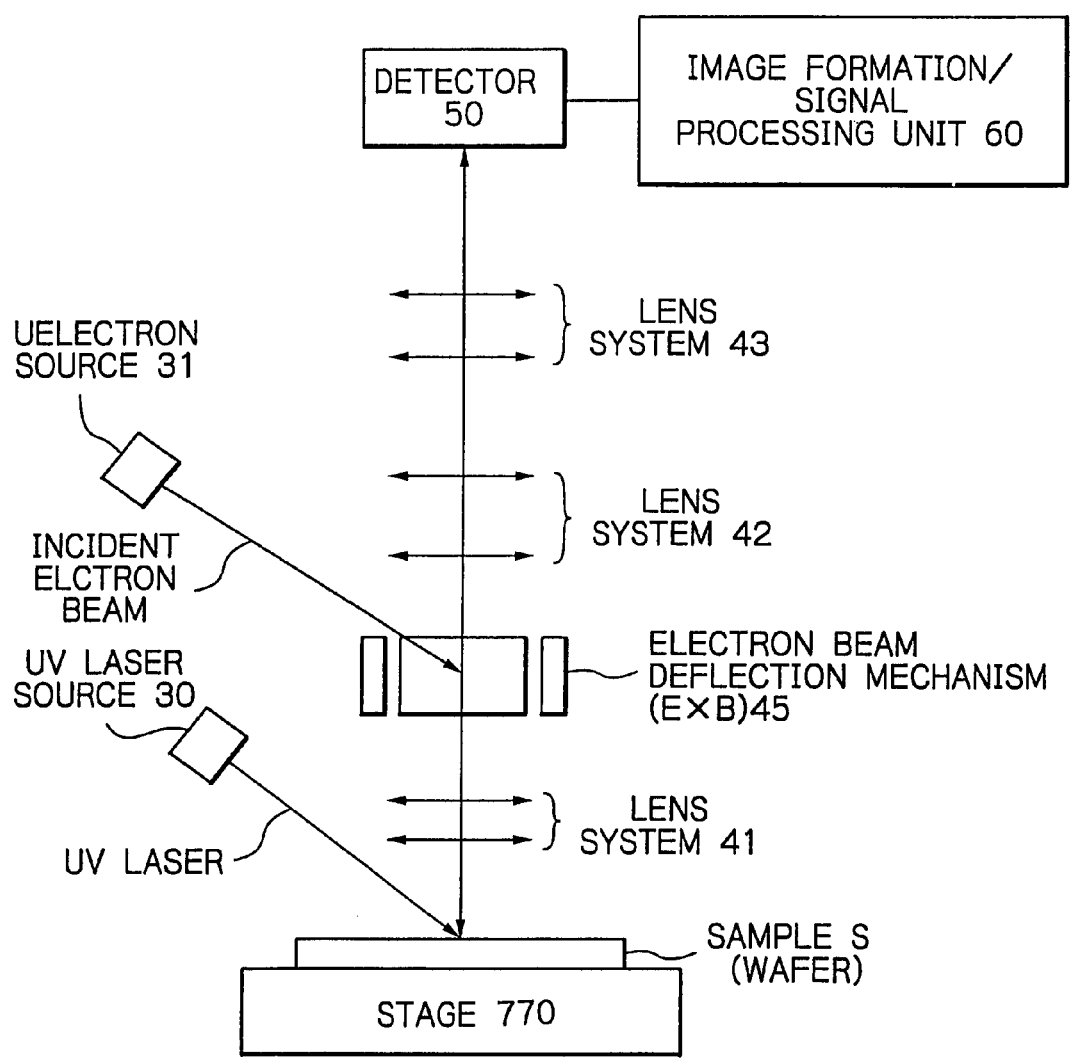
FIG. 18 is a diagram showing a general construction of a fifth embodiment of a surface inspection apparatus (or mechanism) applicable to the system shown in FIG. 9.

FIG. 18 illustrates a fifth embodiment of the inspection mechanism or apparatus 700. In the fifth embodiment, ultraviolet rays and electron beam can be selectively irradiated to a sample surface. The inspection apparatus illustrated in FIG. 16 additionally comprises an electron beam irradiation system including an electron source (electron gun) 31 in addition to the ultraviolet irradiation system including the ultraviolet ray source 30 in the inspection apparatus 700 illustrated in FIG. 16. An ExB deflector (filter) 45 is also provided for deflecting a primary electron beam.

A sample S is a silicon wafer of 8-12 inches which is carried on an X-Y-Z-θ control stage 770. The wafer is formed with circuit patterns of LSI in the middle of manufacturing. A detector 50 used herein can be composed of an electronic amplifier, an opto-electronic converter and a TDI.

The ultraviolet ray source 30 used herein is an Nd:YAG laser based UV laser source for generating fourth-order harmonics (251.5 nm). A UV laser is introduced into a vacuum chamber (not shown) by an appropriate light guide (not shown) for irradiation onto the wafer S within the chamber. An ultraviolet irradiation region is adjusted by optical lenses or the like (not shown) such that the region has a diameter approximately in a range of 0.01 mm to 10 mm. Photoelectrons are generated from the surface of the wafer by the irradiation of ultraviolet rays. The photoelectrons are guided to the detector 50 by the imaging optical system 40.

When the electron beam irradiation is used, electrons generated from the electron source 31 are guided to the surface of the wafer S through a plurality of lenses, aligners and apertures (none of them is shown), and the ExB deflector 45 for deflecting the direction of an electron beam. The electron beam source 31 used herein can be an electron gun which comprises, for example, an LaB$_6$ cathode, a Wehnelt and an anode. A primary electro-optical system can be comprised of an aperture, an aligner, an aperture, a quadruple lens for forming an irradiation beam, an aligner, the ExB deflector and the like. The electron beam thus introduced can be controlled by the primary electro-optical system to have a field of view, the diameter of which is approximately in a range of 10 μm to 1 mm. The irradiation field of view can be formed at an aspect ratio not equal to one, for example, ¼ (=x/y). The energy of the electron beam irradiated to a sample can be selected from a range of approximately 0 to 4 kV.

In the fifth embodiment, the imaging optical system 40 can implement a focus scaling ratio approximately in a range of 50 to 500 by the three lens systems (a total of six lenses). In this event, electrostatic lenses used herein can satisfy the Wien condition in which electrons emitted from the wafer surface travel straight, while an irradiated electron beam is deflected toward the surface.

The detector 50 acquires through the imaging optical system 40 a pattern produced from a difference in the photoelectron generation characteristics (working function and the like) through the irradiation of ultraviolet rays onto the surface of the wafer S, or secondary electrons emitted from the surface of the wafer S irradiated by an electron beam. The electrons from the surface of the wafer S are two-dimensionally detected by the detector 50, and applied to the image formation/signal processing unit 60 for image formation and signal processing. Through the signal processing, the wafer S is evaluated for detecting defects, classifying the defects, and the like.

Likewise, in the fifth embodiment, the surface of the wafer S can be inspected or evaluated sequentially by operating the detector 50 and stage 770 in synchronization. The TDI detector can also detect electron images in sequence while the stage 770 is moved in sequence. The use of this strategy can save a loss time involved in stop/move and loss time until a moving speed is stabilized, as compared with the step & repeat system, thereby efficiently performing evaluations such as detection of defects.

When the inspection mechanism 700 comprises an ultraviolet (or ultraviolet laser) irradiation device and an electron beam irradiation device as in the fifth embodiment, either of the irradiation devices is selected for use with a particular wafer sample, depending on differences in material and structure. For example, when a semiconductor wafer has a structure near the surface which is susceptible to breakdown, such as a gate oxide film, the ultraviolet rays (laser) should be irradiated to the wafer for evaluation. On the other hand, in an evaluation of a wafer Which is flattened after a wiring material has been embedded, when a gate oxide film or the like is away from the surface to an extent enough to be free from damages, an electron beam may be irradiated to acquire a high contrast electron image for evaluating the wafer. In this event, incident energy to the wafer is preferably in a range of 2 to 3 keV.

For materials other than a semiconductor wafer, for example, living samples, polymer materials and the like, ultraviolet ray (laser) irradiation mechanism should be used if an irradiated electron beam would cause charging so strong that the sample could be broken.

Both of the ultraviolet rays and electron beam can be irradiated to a single sample. This method can minimize a potential difference between metal and insulating materials both which are on a sample, to reduce distortions in image. Further, irradiating both the ultraviolet rays and electron beam is also preferable when a larger amount of electrons is desirably acquired from the surface of the sample.

In this event, the sample may be coated with a resist film. When the sample is irradiated with a highly intense electron beam and ultraviolet rays (laser), the resist film coated on the sample can effectively prevent charging, thereby providing a high quality electron image with less distortions.

X-rays or an X-ray laser may be used instead of the ultraviolet rays or ultraviolet laser as well in the fifth embodiment.

Figure 19:
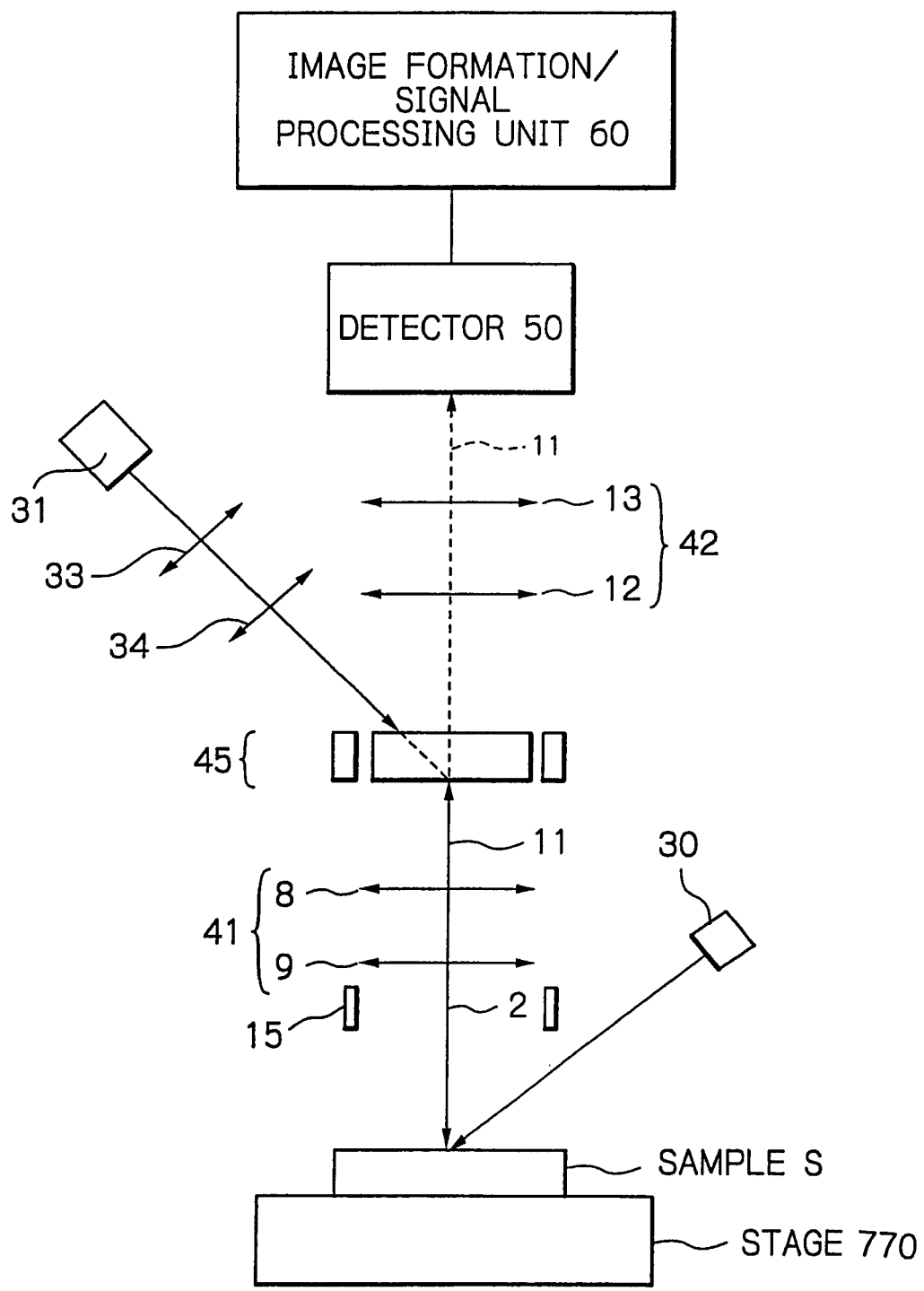
FIG. 19 is a diagram showing a general construction of a sixth embodiment of a surface inspection apparatus (or mechanism) applicable to the system shown in FIG. 9.

FIG. 19 illustrates a sixth embodiment of the inspection mechanism or apparatus 700. In the sixth embodiment, both of ultraviolet ray irradiation and electron beam irradiation are employed. An excimer lamp is used for the ultraviolet ray source 30, and ultraviolet rays from the lamp is irradiated to a surface of a sample S through an appropriate optical system (optical lenses and optical fiber). Electrons emitted from the sample S are guided to the detector through an imaging projection type lens system.

An electron beam emitted from the electron beam source 31 having an electron gun is reshaped by a square aperture, reduced in size by two lenses 33, 34, and focused at the center of a deflection plane of the ExB deflector 45 in the shape of a square, one side of which is 1.25 mm, for instance. The electron beam deflected by the ExB deflector 45 is reduced to ⅕ by lenses 8, 9 (lens system 41) and irradiated onto a sample S.

Electrons (including photoelectrons and secondary electrons) having information of a pattern image, emitted from the sample S, are enlarged by four electrostatic lenses 9, 8, 12, 13 (corresponding to lens systems 41, 42), and detected by the detector 50. The lenses 9, 8 make up a symmetric doublet lens, while the lenses 12, 13 also make up a symmetric doublet lens, thereby providing distortionless lenses. However, since slight distortions may occur due to stains on the electrodes of the lenses, it is preferable that a sample having a standard pattern is used to measure distortions and a parameter is calculated for correcting the distortions.

When the sample S is a wafer Which is selectively formed with an oxide film and a nitride film, a correction for distortions in the optical system is not sufficient. Therefore, when the detector 50 acquire image data, a representative point should be selected from a pattern edge for comparison with the image data for correcting distortions. Then, defects should be detected through a die-by-die comparison or an image-by-image comparison.

In FIG. 19, a control electrode 15 is applied with an appropriately selected voltage to control the field strength on the surface of the sample S, thereby reducing aberration of electrons (secondary electrons and the like) emitted from the surface of the sample S.

Figure 20:
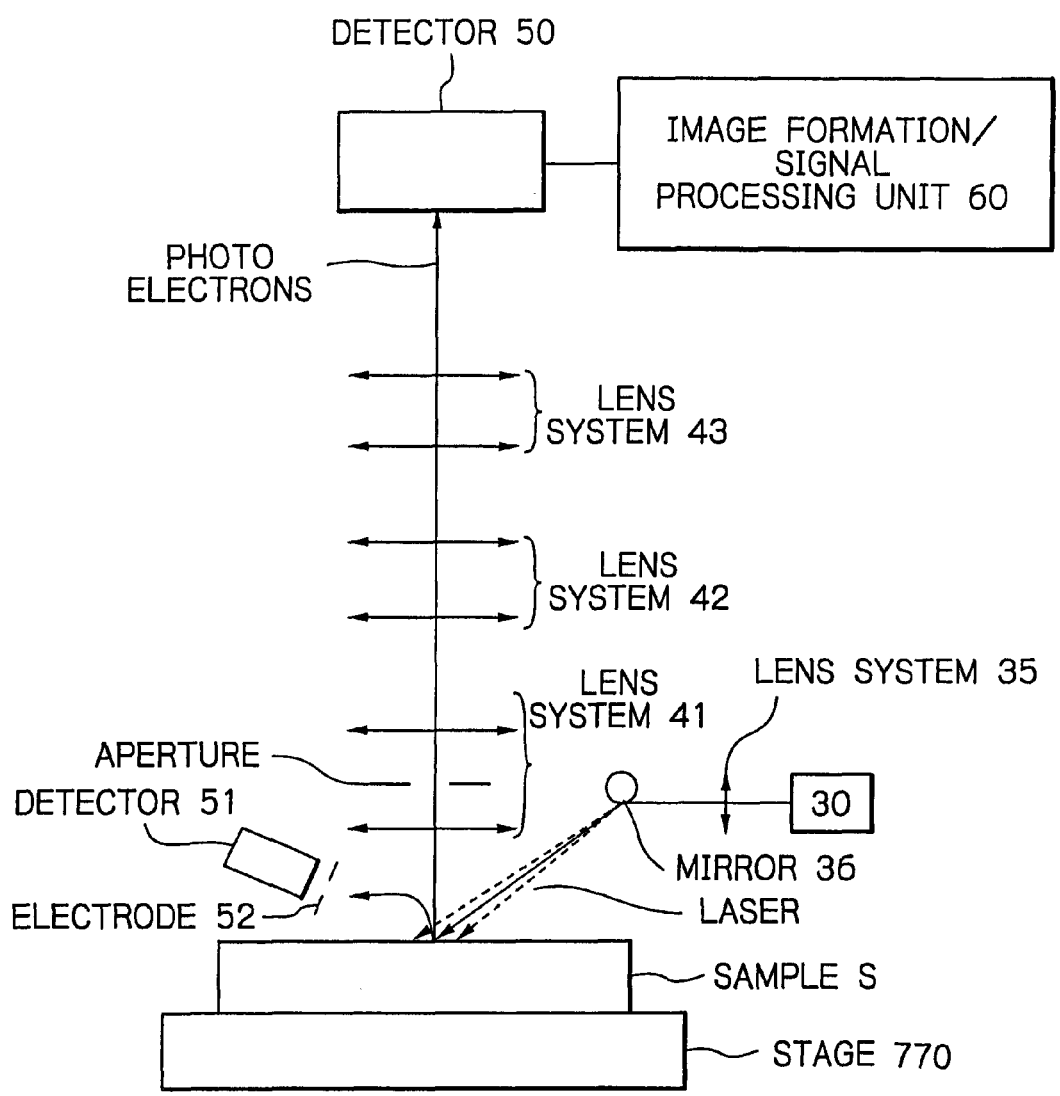
FIG. 20 is a diagram showing a general construction of a seventh embodiment of a surface inspection apparatus (or mechanism) applicable to the system shown in FIG. 9.

FIG. 20 illustrates a seventh embodiment of the inspection mechanism or apparatus 700. In the sixth embodiment, an image detecting system based on laser scanning is employed. The ultraviolet ray source 30 used herein generates a double wave (350-600 nm) or a triple wave (233-400 nm) of a Ti:Al$_2$O$_3$ laser. Generated laser light is guided into a vacuum chamber (not shown) through an optical lens system 35, and is two-dimensionally scanned by a mirror 36 such as a polygon mirror. With the use of the double wave or triple wave of the Ti:Al$_2$O$_3$ laser, a wavelength can be arbitrarily selected in a range of 233 to 600 nm. It is therefore possible to select a wavelength which presents a high photoelectron acquisition efficiency for irradiation in accordance with the material and structure of a sample. Photoelectrons are generated from portions irradiated with the ultraviolet ray laser and detected by a detector 50 which in turn generates an electric signal or an optical signal.

In this event, an image can be generated from the electrons emitted from the sample S in the following two modes:

1) Mode Based on Laser Scan and Imaging Optical System:

Photoelectrons emitted from the surface of the sample S through scanning of the laser light are focused on the detector 50 through the imaging optical system. In this event, the photoelectrons focused on the detector 50 are enlarged by a factor of 50-500 by the imaging optical system while maintaining the coordinates of positions at which the photoelectrons have been two-dimensionally emitted. The detector 50 can be comprised, by way of example, of MCP/FOP/TDI configuration, MCP/fluorescent plate/relay lenses/TDI configuration, EB-TDI configuration, and the like. Also, a CCD may be substituted for the TDI. When the TDI is used, electron images can be acquired while the sample S is moved in sequence by the stage 770. When the CCD is used, electron images are acquired on a step & repeat basis because the CCD acquires still images.

Defects are detected in the images thus acquired in a die-by-die (or chip-by-chip) comparison or a image data based comparison.

2) Mode Based on Laser Scan and Second Detector:

A second detector 51 is an electron detector including a scintillator or a photo-multiplier, which comprises an electrode 52 for attracting photoelectrons. This electrode 52 permits scanning of laser light to be synchronized with an electronic signal, so that a signal from the second detector 51 can be processed into an electron image. Defects on the sample is detected on the electron images produced from secondary electrons acquired by the second detector 51 by the image formation/signal processing unit 60 through a die-by-die comparison or a image data based comparison.

Figure 21:
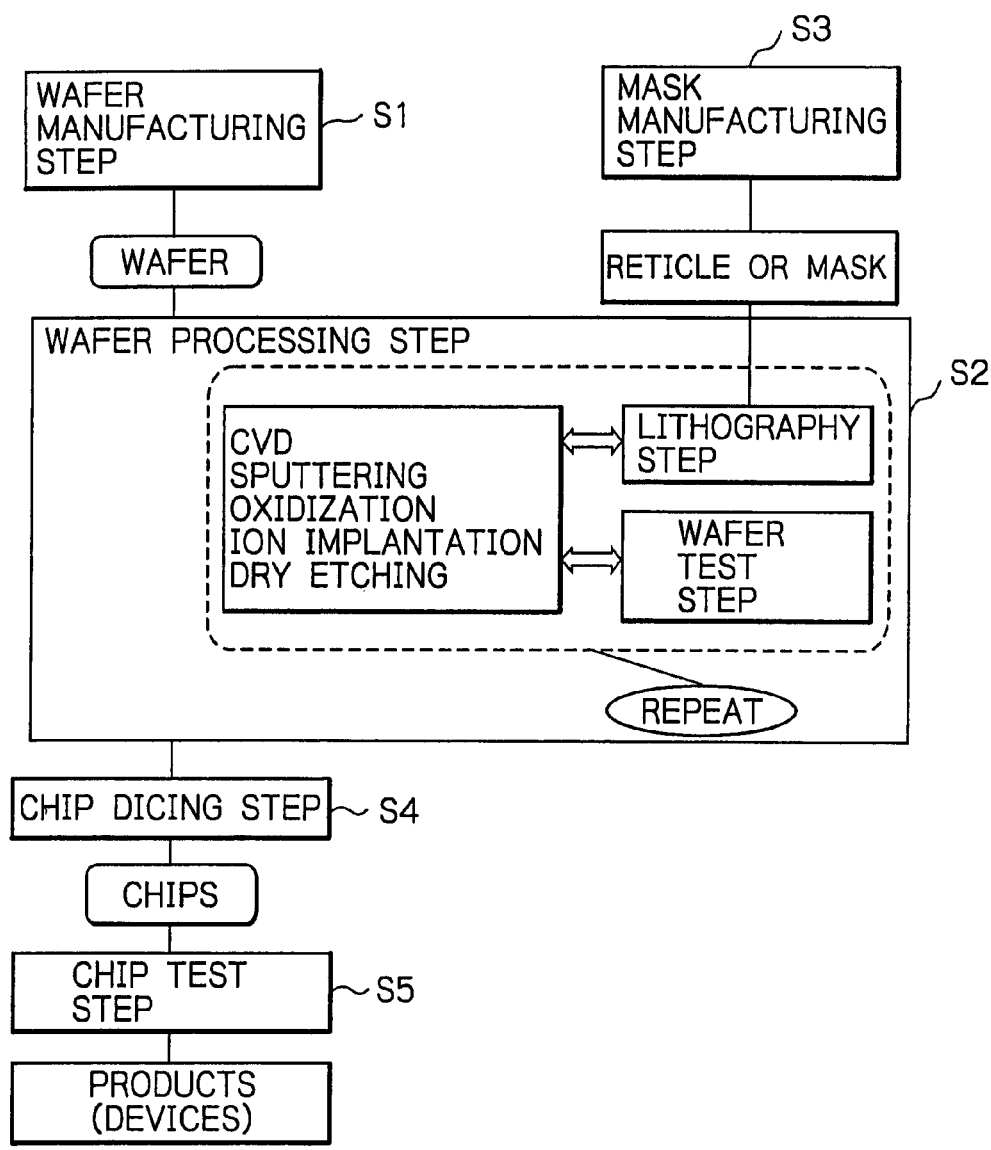
FIG. 21 is a flowchart illustrating a semiconductor device manufacturing method according to the invention.

Next, explanation will be made on a method of manufacturing semiconductor devices which includes procedures for inspecting semiconductor wafers in the middle of a manufacturing process or after the process, using such a surface inspection system as shown in FIG. 9 or such an inspection apparatus as shown in any of FIGS. 14-20. As illustrated in FIG. 21, the method of manufacturing semiconductor devices, when generally divided, comprises the following steps:

1. A wafer manufacturing step S1 for manufacturing wafers (alternatively, a wafer preparing step);
2. A wafer processing step S2 for processing wafers as required;
3. A mask manufacturing step S3 for manufacturing photo masks or reticle masks required for exposure;
4. A chip assembly step S4 for dicing chips formed on a wafer one by one and bringing each chip into an operable state; and
5. A chip testing step S5 for testing finished chips.

Each of the steps S1-S5 may include several sub-steps.

In the respective steps, a step which exerts a critical influence to the manufacturing of semiconductor devices is the wafer processing step S2. This is because designed circuit patterns are formed on a wafer, and a multiplicity of chips which operate as a memory and MPU are formed in this step.

It is therefore important to evaluate a processed state of a wafer executed in sub-steps of the wafer processing steps which influences the manufacturing of semiconductor devices. Such sub-steps will be described below.

First, a dielectric thin film serving as an insulating layer is formed, and a metal thin film is formed for forming wires and electrodes. The thin films are formed by CVD, sputtering or the like. Next, the formed dielectric thin film and metal thin film, and a wafer substrate are oxidized, and a mask (photo mask) or a reticle mask created in the mask manufacturing step S503 is used to form a resist pattern in a lithography step. Then, the substrate is processed in accordance with the resist pattern by a dry etching technique or the like, followed by injection of ions and impurities. Subsequently, a resist layer is stripped off, and the wafer is tested.

The wafer processing step S3 is repeated the number of times equal to the number of required layers to form a wafer before it is separated into chips in the chip assembly step S4.

Figure 22:
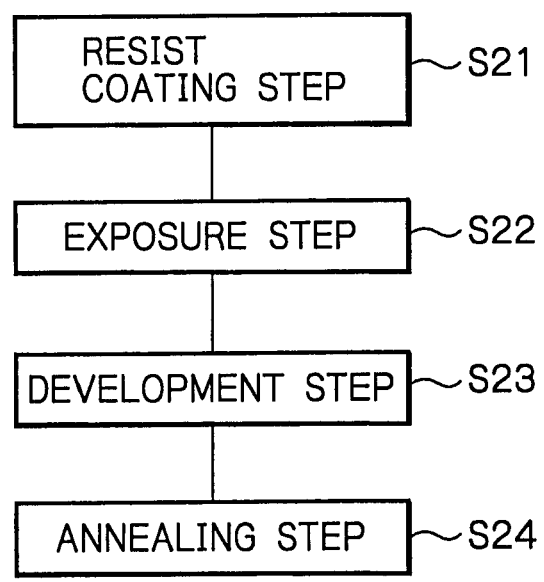
FIG. 22 is a flowchart illustrating a lithography process illustrated in FIG. 21 in greater detail.

FIG. 22 is a flow chart illustrating the lithography step which is a sub-step of the wafer processing step S2 in FIG. 21. As illustrated in FIG. 22, the lithography step includes a resist coating step S21, an exposure step S22, a development step S23, and an annealing step S24.

After a resist is coated on a wafer formed with circuit patterns using CVD or sputtering in the resist coating step S21, the coated resist is exposed in the exposure step S22. Then, in the development step S23, the exposed resist is developed to create a resist pattern. In the annealing step S24, the developed resist pattern is annealed for stabilization. These steps S21 through S24 are repeated the number of times equal to the number of required layers.

In the process of manufacturing semiconductor devices, a test is conducted for defects and the like after the processing step which requires the test. However, the electron beam based defect testing apparatus is generally expensive and is low in throughput as compared with other processing apparatuses, so that the defect testing apparatus is preferably used after a critical step which is considered to most require the test (for example, etching, deposition (including copper plating), CMP (chemical mechanical polishing), planarization, and the like).

In the above-mentioned semiconductor device manufacturing method, a defect in flattening of a sample can be immediately detected and determined, thus enabling efficient process control. The surface inspection apparatus is capable of detecting not only a defect in flattening, but also a failure or a defect in a process prior to flattening. Therefore, process control can be conducted with respect to flattening and other processes conducted prior to flattening. Based on information obtained by this process control, it is possible to efficiently detect, rectify and improve a defect in each process which has been carried out. Further, an entire structure of an inspection apparatus capable of conducting a series of operations between flattening and inspection can be simplified, and samples can be smoothly conveyed using the system illustrated in FIG. 9, thus ensuring a high throughput.

In summary, the present invention is advantageous in the following points.

(1) According to the present invention, a defect in a wafer surface can be correctly measured by suppressing distortion of a measurement image due to electrification. Therefore, it is possible to conduct a scanning operation using a high current, while the electric charge on the wafer can be appropriately controlled, and a large number of secondary electrons can be detected. Therefore, a detection signal having a desirably high S/N ratio can be obtained, thus enabling a defect to be detected with high reliability.

(2) A high S/N ratio can be obtained, and image data can be produced even when scanning is conducted at a high speed. Therefore, a throughput in an inspection apparatus can be increased.

(3) When an electron beam or an ion beam is emitted to a wafer, in the case where the beam has energy as high as about 2 keV or more, there is a possibility of a substrate or device circuits formed thereon being damaged. This possibility can be reduced by effecting observation or inspection according to the present invention. While high beam energy causes device damage in conventional techniques, such damage does not occur in the present invention and an electron image having minimum distortion can be obtained.

(4) A defect in flattening of a wafer can be immediately detected and determined, thus enabling efficient process control. The surface inspection apparatus of the present invention is capable of detecting not only a defect in flattening, but also a failure or a defect in a process prior to flattening. Therefore, process control can be conducted with respect to flattening and other processes conducted prior to flattening. Based on information obtained by this process control, it is possible to efficiently detect, rectify and improve a defect in each process which has been carried out. Further, a yield of a device manufacturing process can be increased, and a cost of manufacture of devices can be reduced.

(5) In order to provide the above advantage, it is possible to use an image processing system capable of determining the types of defects generated in wafer surfaces. This image processing system is capable of determining, for example, deposition of a foreign matter, contact failure in circuits, and a defect in a pattern form. Therefore, it is possible to determine, from an acquired electron image, in which manufacturing process or which place in an apparatus a defect was generated. Thus, a cause of a defect can be efficiently improved and rectified.

(6) According to the present invention, it has become possible to manufacture devices by a method in which a defect in a wafer during a process is detected by using the above-mentioned inspection apparatus and method.

(7) Loading/unloading robots, such as those used in a conventional independent apparatuses, can be eliminated, thus simplifying an entire structure of the apparatus and reducing a size of the apparatus. Further, a process for conveyance of a wafer can be simplified, thus increasing a throughput.

(8) The respective mechanisms of the inspection apparatus are disposed on a single base. Therefore, it is easy to conduct adjustment of a work position of a wafer and a loading/unloading position, which is difficult in a conventional system in which a plurality of independent apparatuses are placed.

(9) The number of utilities and control valves for supplying compressed air, electricity, cooling water, pure water or ultrapure water, a nitrogen gas, etc, can be reduced. Therefore, the inspection apparatus can be simplified.

(10) The possibility of exposing a wafer to an external environment can be reduced, thus preventing contamination of wafers.

Although the present invention has been described above in detail with reference to the drawings, the foregoing description is for explanatory purposes and not intended to limit characteristics. It should be understood that the foregoing description merely illustrates and explains preferred embodiments, and all modifications and changes within the scope of the spirit of the present invention are protected.

We claim:

1. A mechanism for inspecting a surface of a sample, comprising:
an electro-optical inspection apparatus comprising:
an electromagnetic wave source for irradiating the sample surface with electromagnetic waves;
an electron source consisting of an electron gun for emitting an electron beam in a direction which is not perpendicular to the sample surface; and
an EXB deflector for deflecting the electron beam emitted from the electron source to irradiate the sample surface therewith in a direction which is perpendicular to the sample surface, and passing photoelectrons emitted from the sample surface when it is irradiated with the electromagnetic waves, and electrons from the sample surface when it is irradiated with the electron beam;
a detector for detecting the photoelectrons and electrons, respectively which are passed through the EXB deflector to output electric signals associated with the detected photoelectrons and electrons, respectively; and
a processing unit for processing the signals output from the detector and forming an image associated with the sample surface.

2. A mechanism according to claim 1, wherein the electro-optical inspection apparatus further comprises an objective lens system comprising at least two lenses located between the sample surface and the EXB deflector, and an enlarging lens system comprising at least two lenses and located between the EXB deflector and the detector.

3. A mechanism according to claim 1, wherein the electro-optical inspection apparatus further comprises an objective lens system comprising at least two lenses located between the sample surface and the FXB deflector, and two enlarging lens systems each comprising at least two lenses and located between the EXB deflector and the detector.

4. A mechanism according to claim 1, wherein the electro-optical inspection apparatus is an image projection type inspection apparatus.

5. A mechanism according to claim 1, wherein a diameter of the electromagnetic waves irradiated on the sample surface is in a range of about 10 μm-10 mm.

6. A mechanism according to claim 1, a diameter of a field of view of the electron beam is about 10 μm-10 mm.

7. A mechanism according to claim 1, further comprising a control electrode to supply a voltage to control a field strength on the sample surface, to thereby reduce aberration of the photoelectrons or electrons emitted from the sample surface.

8. A mechanism according to claim 1, wherein the sample is at least one of a semiconductor wafer with a resistive film thereon, a photo-mask and reticle-mask.

9. A mechanism according to claim 1, wherein the electromagnetic wave source irradiates the sample surface with the electromagnetic waves in a direction which is not perpendicular to the sample surface.

10. A method of inspecting a surface of a sample, comprising:
  actuating one or both of the electromagnetic wave source and the electron source in accordance with a kind of the sample;
  irradiating the sample surface with one or both of the electromagnetic waves and the electron beam which are/is emitted from the actuated source;
  detecting either of photoelectrons and electrons emitted from the sample surface by the detector to output the signal; and
  processing the signal by the processing unit to obtain an image of the sample surface.

11. A method according to claim 10, wherein the sample surface is coated with a resistive film.

* * * * *